(12) United States Patent
Lee et al.

(10) Patent No.: US 11,987,566 B2
(45) Date of Patent: May 21, 2024

(54) NERVE DAMAGE PREVENTING AND NERVE PROTECTING COMPOUNDS, PREPARATION METHOD THEREOF, PHARMACEUTICAL COMPOSITION THEREOF, AND THEIR USE

(71) Applicant: GENHEALTH PHARMA CO., LTD., Taipei (TW)

(72) Inventors: Lain-Tze Lee, Hsinchu (TW); Hui-Ping Tsai, Hsinchu (TW); Yi-Wen Lin, Taoyuan (TW); Shu-Fen Huang, Taoyuan (TW); Shih-Hung Liu, Taoyuan (TW); Chin-Wei Liu, Taoyuan (TW); Pi-Tsan Huang, Hsinchu (TW); Mei-Hui Chen, Hsinchu (TW)

(73) Assignee: GENHEALTH PHARMA CO., LTD., Taipei (TW)

( * ) Notice: Subject to any disclaimer, the term of this patent is extended or adjusted under 35 U.S.C. 154(b) by 0 days.

(21) Appl. No.: 17/587,268

(22) Filed: Jan. 28, 2022

(65) Prior Publication Data
US 2023/0242501 A1 Aug. 3, 2023

(51) Int. Cl.
*C07D 317/64* (2006.01)
*A61P 25/28* (2006.01)
*C07D 317/68* (2006.01)
*C07D 405/12* (2006.01)
*C07D 409/12* (2006.01)

(52) U.S. Cl.
CPC ............ *C07D 317/64* (2013.01); *A61P 25/28* (2018.01); *C07D 317/68* (2013.01); *C07D 405/12* (2013.01); *C07D 409/12* (2013.01)

(58) Field of Classification Search
CPC .. C07D 317/64; C07D 317/68; C07D 405/12; C07D 409/12
See application file for complete search history.

(56) References Cited

FOREIGN PATENT DOCUMENTS

| EP | 3415145 A2 | 12/2018 |
| JP | 2012-017294 A | 1/2012 |
| TW | 201141474 A | 12/2011 |
| TW | 201902474 A | 1/2019 |
| TW | 202038981 A | 11/2020 |

OTHER PUBLICATIONS

Yin et al. Journal of Ethnopharmacology 2016, 188, 229-233 (Year: 2016).*
Barrero et al. Phytochemistry 1994, 37, 1351-1358 (Year: 1994).*
Tsyganov et al. ACS Omega 2022, 7, 3369-3383 (Year: 2022).*
Registry No. 120-80-9, entered STN on Nov. 16, 1984 (Year: 1984).*
Pan et al. Synthesis, 1980, pp. 813-814 (Year: 1980).*
CAS Registry Entry No. 1020245-18-4, which entered STN on May 11, 2008 (Year: 2008).*
CAS Registry Entry No. 1011406-27-1, which entered STN on Apr. 1, 2008 (Year: 2008).*
CAS Registry Entry No. 948010-46-6, which entered STN on Sep. 25, 2007 (Year: 2007).*
CAS Registry Entry No. 948010-41-1, which entered STN on Sep. 25, 2007 (Year: 2007).*
Han et al. J. Korean. Med. Sci. 2014, 29, 886-892 (Year: 2014).*
Hanbali et al. "Quinol fatty alcohols as promoters of axonal growth", Bioorganic(2006).
Varakutin et al. "Hydrogenation of plant polyalkoxybenzene derivatives convenient access to coenzyme Q analogues", Mendeleev(2020).
Athikomkulchai et al. "Chemical composition of essential oil from piper sarmentosum fruit and neuroprotective activity", Tropical Journal(2021).
Tsyganov et al. "Synthesis and antiproliferative activity triphenylphosphonium derivatives of natural allylpolyalkoxybenzenes", ACS(2022).
Barrero et al. "Sesquiterpene lactones and other constituents of seseli vayredanum" Phytochemistry(1994).
PubChem No. 91735764(2015), http://pubchem.ncbi.nlm.nih.gov/compound/91735764#section=identification-and-related-records.
PubChem No. 16766927(2007), http://pubchem.ncbi.nlm.nih.gov/compound/16766927#section=identification-and-related-records.
PubChem No. 26433746(2009), http://pubchem.ncbi.nlm.nih.gov/compound/26433746#section=identification-and-related-records.
PubChem No. 56640465(2012), http://pubchem.ncbi.nlm.nih.gov/compound/56640465#section=identification-and-related-records.
Shi e al. "Biologically Active constituents from the fruiting body of Taiwanofungus camphoratus" Bioorg.Med.Chem (2011), Elsevier.
Dallacker et al. "Uber Polyencarbonsaureimide des Methylendioxybenzols" Chem.Ber (1975).
Dallacker et al. "Darstellung von substituierten Dihydronaphthalincarbaldehyden" Chem.Ber (1980).
Yeung et al. "Antiprofliferative activity of the Antrodia camphorata secondary metabolite 4, 7-dimethoxy-5-methylbenzo [d][1,3] dioxole and analogues", Fitoterapia (2017), Elsevier.
Rizzacasa et al."The Structure and Synthesis of Nepenthone-A, a Naphthoquninone from Nepenthes rafflesiana" J. Chem.Soc.Perkin Trans. 1 (1987).
Tsyganov et al. "Journal of Nature Products" (2013), ACS Publications.
Registry of STN (2007, 2008).
Pan et al. "A Facile, Rapid Preparation of a series of Cinnamyl Alcohols from 3-Phenylpropenes using Selenium Dioxide" Synthesis October (1980), Georg Theime Verlag, New York.
Dallacker et al. "Derivate des .3-Benzdioxols, 51[1]" Z.Naturforsch (1984).
Six CAS Registry Chemicals, No. 1020245-18-4 (May 11, 2008), No. 1011406-27-1 (Apr. 1, 2008), No. 948010-46-6 (Sep. 25, 2007), No. 948010-41-1 (Sep. 25, 2007), No. 1020242-83-4 (May 11, 2008).

(Continued)

Primary Examiner — Matthew P Coughlin
(74) Attorney, Agent, or Firm — WPAT, PC

(57) ABSTRACT

The present invention provides a novel compound for effectively preventing nerve damage and protecting nerves, and a preparation method thereof. Besides, the present invention also provides a pharmaceutical composition comprising the novel compound, and a use of the novel compound for preventing nerve damage and protecting nerves.

11 Claims, 4 Drawing Sheets

(56) References Cited

OTHER PUBLICATIONS

Tsyganov, D. V. et al., cis-Restricted 3-aminopyrazole analogues of combretastatins: synthesis from plant polyalkoxybenzenes and biological evaluation in the cytotoxicity and phenotypic sea urchin embryo assays, Tsyganov D.V. et al, Journal of Natural Products, vol. 76, No. 8, pp. 1485-1491 (2013).
Dallacker, F. et al., Derivatives of Methylenedioxybenzene, 34, On the Preparation of Dimethoxy(methylenedioxy) benzenedicarboxylic Acids, Dallacker F. et al, Chemical Reports, vol. 113, No. 4, pp. 1320-1327 (1971).
Dallacker, F., Derivatives of Methylenedioxy-benzene, XXVIII.: Reactions of the Dimethoxy-methylendioxy-benzaldehydes, Dallacker F. et al, monthly journals for chemistry, vol. 100, No. 2, pp. 742-747 (1969).
PubChem No. 16767154 (Nov. 13, 2007).

\* cited by examiner

NERVE DAMAGE PREVENTING AND NERVE PROTECTING COMPOUNDS, PREPARATION METHOD THEREOF, PHARMACEUTICAL COMPOSITION THEREOF, AND THEIR USE

BACKGROUND OF THE INVENTION

1. Field of the Invention

The present invention relates to a compound, a preparation method thereof, a pharmaceutical composition thereof, and their use, and more particularly to a nerve damage preventing and nerve protecting compound, a preparation method thereof, a pharmaceutical composition comprising the same, and their use for preventing nerve damage and protecting nerves.

2. Description of the Prior Arts

Diseases caused by nerve degeneration or nerve damage usually have long-term influence on patient's life quality. However, effective and non-invasive treatment of foresaid diseases has been lacking up to now. Currently, medicines effective for preventing nerve damage and protecting nerves of the nervous system from the related diseases, such as stroke, brain ischemia, brain damage, Alzheimer's disease, Parkinson's disease and retinopathy, become the major research in the related fields.

Nervous tissue consists of neurons and neuroglia. Because of the weak regeneration ability of neurons, how to promote neuron regeneration and protect neurons from secondary injury after nervous system damage is an important topic in clinical treatment.

The molecular mechanism of neuron damage comprises: calcium overload caused by numerous calcium intake, massive release of excitatory amino acids, and the direct neuron damage coming from free radical and inflammation.

In recent years, okadaic acid (OKA) is used to build up a nerve damage model for studying the nerve degeneration diseases and Alzheimer's disease. Okadaic acid is an inhibitor of protein phosphatase 1 (PP1) and protein phosphatase 2 (PP2 or PP2A). As PP1 and PP2A are able to reduce the phosphorylation level of tau protein, okadaic acid can inhibit PP1 and PP2A and induces more phosphorylation on tau protein to build up a model of Alzheimer's disease, which can be used to verify the efficacy of the medicine in the treatment of Alzheimer's disease.

Nowadays, there are more choices of the medicines for senile dementia caused by Alzheimer's disease. The medicines of anti-cholinesterase such as Donepezil, Rivastigmine and Galantamine are used in mild to moderate dementia cases; while in moderate to severe dementia cases, the medicines such as foresaid Donepezil and NMDA antagonist, e.g., Memantine, can be used.

On the other hand, the treatment options for ischemia stroke are limited. However, ischemia stroke is the main cause of death and disability. In general, when stroke or brain injury leads to ischemia brain damage, and subsequently the secondary damage caused by blood reperfusion, the brain nerves will die in a few days to a few months. Specifically, when the ischemia-reperfusion occurred in the brain nervous tissue, it will produce numerous reactive oxygen species (ROS) and cause calcium intake, which induces the inflammation mechanism to activate cytokine and leukocyte to infiltrate into the ischemia area, thereby inducing inflammation and leading to brain nervous tissue damage.

So for, the medicines commonly used for ischemia stroke include antiplatelet agents that have the effect of anti-thrombosis, such as Clopidogrel, Aspirin, Ticlopidine and Dipyridamole; anticoagulants that used to prevent thrombosis and reducing the expansion of thrombus and the production of embolism, such as heparin, low molecular weight heparin and Warfarin; thrombolytic agents that induce fibrin decomposition, such as Urokinase and recombinant tissue plasminogen activator (rtPA); medicines for preventing hydrocephalus caused by severe stroke, such as mannitol and glycerol; and medicines that prevent massive necrosis of brain neurons by controlling calcium channel, scavenging the free radicals and reducing the metabolic rate of brain cells in the ischemia area, such as Piracetam and Nimodipine.

Nevertheless, the clinical effects of the foresaid medicines for preventing and treating the nerve related diseases is still not satisfactory. Therefore, there is an urgent need to find and develop methods for effectively preventing nerve damage and protecting nerves in both industrial and clinic practices, so as to provide patients with more diverse medical treatment options.

SUMMARY OF THE INVENTION

According to the aforementioned shortcomings, the present invention provides a novel compound that has effects of preventing nerve damage and protecting nerves.

To achieve the aforementioned objective, the present invention provides a compound represented by the following Formula (I):

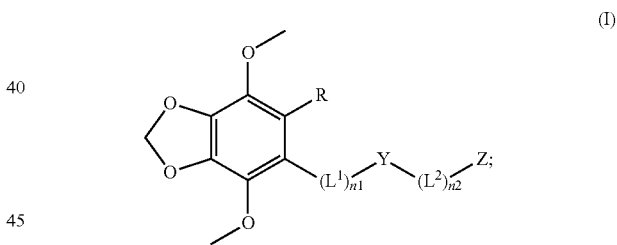

wherein, R is a hydrogen atom or an unsubstituted alkyl group having 1 to 6 carbon atoms;

$L^1$ is an unsubstituted alkylene group having 1 to 6 carbon atoms, and $L^2$ is an unsubstituted alkylene group having 1 to 6 carbon atoms or an unsubstituted arylene group having 6 to 18 carbon atoms;

Y is an unsubstituted alkylene group having 1 to 6 carbon atoms, an unsubstituted alkenylene group having 2 to 6 carbon atoms, an acyloxy group, or an amide group;

Z is a hydroxyl group, a carboxyl group, an unsubstituted alkyl group having 1 to 6 carbon atoms, a dihydroxybenzyl group, an unsubstituted ester group having 1 to 6 carbon atoms, an unsubstituted aryl group having 6 to 18 carbon atoms, 2-methoxybenzenesulfonamide, 2,3-dimethyl-1-phenyl-5-pyrazolone, or 2-methyl-4-cyanothiophene; and n1 and n2 are each independently 0 or 1.

In this specification, the description "alkyl group having 1 to 6 carbon atoms" may be a linear or a branched alkyl group, which indicates that the whole functional group has 1 to 6 carbon atoms in total. For example, the alkyl group having 1 to 6 carbon atoms may be, but is not limited to, a methyl group (—CH$_3$), an ethyl group (—CH$_2$CH$_3$), a n-propyl group (—CH$_2$CH$_2$CH$_3$), an isopropyl group (—CH (CH$_3$)$_2$), a n-butyl group (—CH$_2$CH$_2$CH$_2$CH$_3$), an isobutyl group (—CH$_2$CH(CH$_3$)$_2$), a sec-butyl group (—CH(CH$_3$) CH$_2$CH$_3$), or a tert-butyl group (—C(CH$_3$)$_3$). Specifically, the foresaid alkyl group having 1 to 6 carbon atoms may be an alkyl group having 1, 2, 3, 4, 5, or 6 carbon atoms.

In this specification, the term "alkylene group having 1 to 6 carbon atoms" may be, but is not limited to, a methylene group (—CH$_2$—), an ethylene group (—CH$_2$CH$_2$— or —CH(CH$_3$)—), a propylene group (—CH$_2$CH$_2$CH$_2$—, —CH$_2$CH(CH$_3$)— or —C(CH$_3$)$_2$—), or a butylene group (e.g., —CH$_2$CH$_2$CH$_2$CH$_2$—, —CH$_2$C(CH$_3$)$_2$— or —CH (CH$_3$)CH$_2$CH$_2$—). Specifically, the foresaid alkylene group having 1 to 6 carbon atoms may be an alkylene group having 1, 2, 3, 4, 5, or 6 carbon atoms.

In this specification, the term "alkenylene group having 2 to 6 carbon atoms" indicates that the whole functional group has 2 to 6 carbon atoms in total. For example, the alkenylene group having 2 to 6 carbon atoms may be, but is not limited to, a vinylene group (e.g., —CH═CH—), a propenylene group (e.g., —CH$_2$CH═CH— or —CH═C(CH$_3$)—), or a butenylene group (e.g., —CH$_2$CH═CHCH$_2$— or —CH═CHCH$_2$CH$_2$—). Specifically, the foresaid alkenylene group having 2 to 6 carbon atoms may be an alkenylene group having 2, 3, 4, 5, or 6 carbon atoms.

In this specification, the term "arylene group having 6 to 18 carbon atoms" indicates that the ring structure of the whole functional group has 6 to 18 carbon atoms in total. For example, the arylene group having 6 to 18 carbon atoms may be, but is not limited to, a phenylene group (—C$_6$H$_4$—), a biphenylene group (—C$_6$H$_4$-C$_6$H$_4$—), or a naphthylene group (—C$_{10}$H$_6$—). Specifically, the foresaid arylene group having 6 to 18 carbon atoms may be an arylene group having 6, 7, 8, 9, 10, 11, 12, 13, 14, 15, 16, 17 or 18 carbon atoms.

Specifically, in Formula (I), the phenylene group may be ortho-phenylene group, meta-phenylene group, or para-phenylene group. Preferably, the phenylene group is para-phenylene group.

Specifically, in Formula (I), the dihydroxybenzyl group may be pyrocatechin, resorcinol, or hydroquinone. Preferably, the dihydroxybenzyl group is pyrocatechin.

Preferably, Y is an unsubstituted ethylene group, an unsubstituted propylene group, an unsubstituted butylene group, an unsubstituted propenylene group, an acyloxy group, or an amide group.

Preferably, Z is a hydroxyl group, a carboxyl group, a methyl group, pyrocatechin, —COOCH$_2$CH$_3$, an unsubstituted phenyl group, 2-methoxybenzenesulfonamide, 2,3-dimethyl-1-phenyl-5-pyrazolone, or 2-methyl-4-cyanothiophene.

Preferably, L$^2$ is an unsubstituted methylene group, an unsubstituted ethylene group, an unsubstituted propylene group, or an unsubstituted phenylene group.

Specifically, in Formula (I), Y may be represented by a*-Y-b*, and the a* and the b* indicate two different attachment sites of Y. That is, Y may attach to L$^1$ through the a* and attach to L$^2$ through the b*, or Y may attach to L$^2$ through the a* and attach to L$^1$ through the b*.

In some embodiments of the present invention, Y is an acyloxy group, and attaches to L$^1$ with the oxygen atom thereof through the a*, and attached to L$^2$ with the carbon atom thereof through the b*; L$^1$ is an unsubstituted alkylene group having 1 to 6 carbon atoms, and n1 is 0 or 1; L$^2$ is an unsubstituted alkylene group having 1 to 6 carbon atoms or an unsubstituted arylene group having 6 to 18 carbon atoms, and n2 is 0 or 1; Z is a hydroxyl group or an unsubstituted alkyl group having 1 to 6 carbon atoms; and R is a hydrogen atom or an unsubstituted alkyl group having 1 to 6 carbon atoms. In those embodiments, compounds are represented by the following Formula (i):

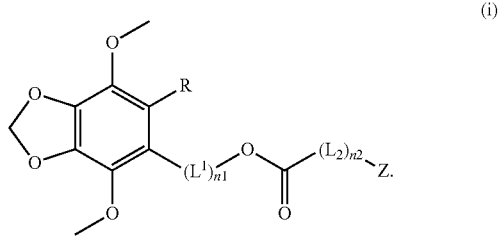

In some embodiments of the present invention, Y is an acyloxy group, and Y attaches to L$^1$ with the oxygen atom thereof through the a* and attaches to L$^2$ with the carbon atom thereof through the b*; L$^1$ is an unsubstituted alkylene group having 1 to 6 carbon atoms, and n1 is 1; n2 is 0; Z is an unsubstituted alkyl group having 1 to 6 carbon atoms; and R is a hydrogen atom. In those embodiments, compounds are represented by the following Formula (ii):

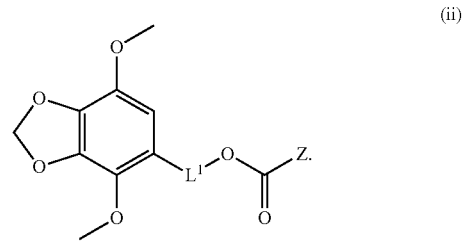

In some embodiments of the present invention, Y is an acyloxy group, and Y attaches to L$^2$ with the oxygen atom thereof through the a* and attaches to L$^1$ with the carbon atom thereof through the b*; L$^1$ is an unsubstituted alkylene group having 1 to 6 carbon atoms, and n1 is 0 or 1; n2 is 0; Z is an unsubstituted alkyl group having 1 to 6 carbon atoms, a dihydroxybenzyl group, an unsubstituted aryl group having 6 to 18 carbon atoms, 2-methoxybenzenesulfonamide, 2,3-dimethyl-1-phenyl-5-pyrazolone, or 2-methyl-4-cyanothiophene; and R is a hydrogen atom or an unsubstituted alkyl group having 1 to 6 carbon atoms. In those embodiments, compounds are represented by the following Formula (iii):

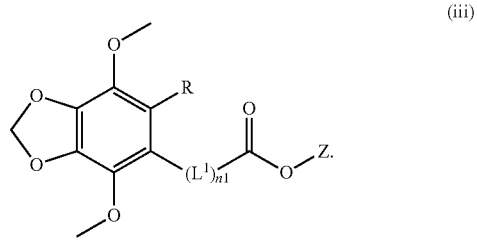

In some embodiments of the present invention, Y is an acyloxy group, and Y attaches to L$^2$ with the oxygen atom thereof through the a* and attaches to L$^1$ with the carbon atom thereof through the b*; L¹ is an unsubstituted alkylene group having 1 to 6 carbon atoms, and n1 is 0 or 1; L² is an unsubstituted alkylene group having 1 to 6 carbon atoms, and n2 is 1; Z is a hydroxyl group, a carboxyl group, an unsubstituted alkyl group having 1 to 6 carbon atoms, a dihydroxybenzyl group, an unsubstituted ester group having 1 to 6 carbon atoms, an unsubstituted aryl group having 6 to 18 carbon atoms, 2-methoxybenzenesulfonamide, 2,3-dimethyl-1-phenyl-5-pyrazolone, or 2-methyl-4-cyanothiophene; and R is a hydrogen atom or an unsubstituted alkyl group having 1 to 6 carbon atoms. In those embodiments, compounds are represented by the following Formula (iv):

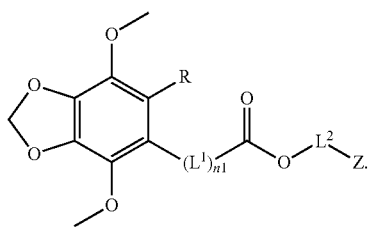

(iv)

In some embodiments of the present invention, compounds are represented by the above Formula (iv), and L¹ is an unsubstituted alkylene group having 1 to 6 carbon atoms, and n1 is 0 or 1; L² is an unsubstituted arylene group having 6 to 18 carbon atoms, and n2 is 1; Z is a hydroxyl group, a carboxyl group, an unsubstituted alkyl group having 1 to 6 carbon atoms, or an unsubstituted ester group having 1 to 6 carbon atoms; and R is a hydrogen atom or an unsubstituted alkyl group having 1 to 6 carbon atoms.

In some embodiments of the present invention, Y is an acyloxy group, and Y attaches to L² with the oxygen atom thereof through the a* and attaches to L¹ with the carbon atom thereof through the b*; n1 is 0; L² is an unsubstituted alkylene group having 1 to 6 carbon atoms, and n2 is 1; Z is an unsubstituted aryl group having 6 to 18 carbon atoms; and R is a hydrogen atom. In those embodiments, compounds are represented by the following Formula (v):

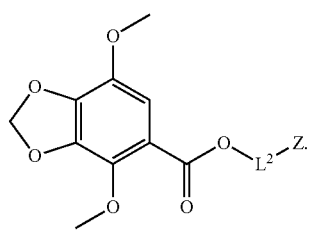

(v)

In some embodiments of the present invention, Y is an amide group, and Y attaches to L¹ with the nitrogen atom thereof through the a* and attaches to L² with the carbon atom thereof through the b*; L¹ is an unsubstituted alkylene group having 1 to 6 carbon atoms, and n1 is 0 or 1; L² is an unsubstituted alkylene group having 1 to 6 carbon atoms or an unsubstituted arylene group having 6 to 18 carbon atoms, and n2 is 0 or 1; Z is a hydroxyl group or an unsubstituted alkyl group having 1 to 6 carbon atoms; and R is a hydrogen atom or an unsubstituted alkyl group having 1 to 6 carbon atoms. In those embodiments, compounds are represented by the following Formula (vi):

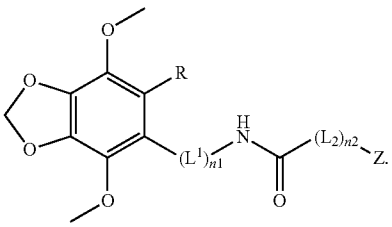

(vi)

In some embodiments of the present invention, Y is an amide group, and Y attaches to L¹ with the nitrogen atom thereof through the a* and attaches to L² with the carbon atom thereof through the b*; L¹ is an unsubstituted alkylene group having 1 to 6 carbon atoms, and n1 is 1; n2 is 0; Z is an unsubstituted alkyl group having 1 to 6 carbon atoms; and R is a hydrogen atom. In those embodiments, compounds are represented by the following Formula (vii):

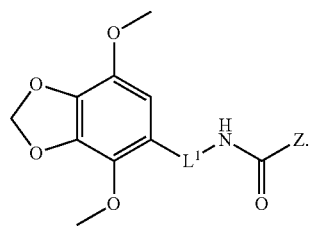

(vii)

In some embodiments of the present invention, Y is an amide group, and Y attaches to L² with the nitrogen atom thereof through the a* and attaches to L¹ with the carbon atom thereof through the b*; L¹ is an unsubstituted alkylene group having 1 to 6 carbon atoms, and n1 is 0 or 1; n2 is 0; Z is an unsubstituted alkyl group having 1 to 6 carbon atoms, a dihydroxybenzyl group, an unsubstituted aryl group having 6 to 18 carbon atoms, 2-methoxybenzenesulfonamide, 2,3-dimethyl-1-phenyl-5-pyrazolone, or 2-methyl-4-cyanothiophene; and R is a hydrogen atom or an unsubstituted alkyl group having 1 to 6 carbon atoms. In those embodiments, compounds are represented by the following Formula (viii):

(viii)

In some embodiments of the present invention, Y is an amide group, and Y attaches to L² with the nitrogen atom thereof through the a* and attaches to L¹ with the carbon atom thereof through the b*; n1 is 0; n2 is 0; Z is 2,3-dimethyl-1-phenyl-5-pyrazolone or 2-methyl-4-cyanothiophene; and R is a hydrogen atom. In those embodiments, compounds are represented by the following Formula (ix):

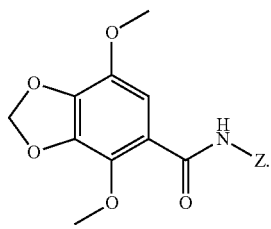

(ix)

In some embodiments of the present invention, Y is an amide group, and Y attaches to $L^2$ with the nitrogen atom thereof through the a* and attaches to $L^1$ with the carbon atom thereof through the b*; $L^1$ is an unsubstituted alkylene group having 1 to 6 carbon atoms, and n1 is 0 or 1; $L^2$ is an unsubstituted alkylene group having 1 to 6 carbon atoms, and n2 is 1; Z is a hydroxyl group, a carboxyl group, an unsubstituted alkyl group having 1 to 6 carbon atoms, a dihydroxybenzyl group, an unsubstituted ester group having 1 to 6 carbon atoms, an unsubstituted aryl group having 6 to 18 carbon atoms, 2-methoxybenzenesulfonamide, 2,3-dimethyl-1-phenyl-5-pyrazolone, or 2-methyl-4-cyanothiophene; and R is a hydrogen atom or an unsubstituted alkyl group having 1 to 6 carbon atoms. In those embodiments, compounds are represented by the following Formula (x):

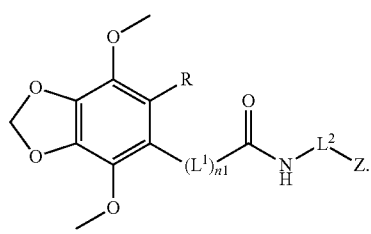

(x)

In some embodiments of the present invention, compounds are represented by the above Formula (x), and $L^1$ is an unsubstituted alkylene group having 1 to 6 carbon atoms, and n1 is 0 or 1; $L^2$ is an unsubstituted arylene group having 6 to 18 carbon atoms, and n2 is 1; Z is a hydroxyl group, a carboxyl group, an unsubstituted alkyl group having 1 to 6 carbon atoms, or an unsubstituted ester group having 1 to 6 carbon atoms; and R is a hydrogen atom or an unsubstituted alkyl group having 1 to 6 carbon atoms.

In some embodiments of the present invention, Y is an amide group, and Y attaches to $L^2$ with the nitrogen atom thereof through the a* and attaches to $L^1$ with the carbon atom thereof through the b*; n1 is 0; $L^2$ is an unsubstituted alkylene group having 1 to 6 carbon atoms, and n2 is 1; Z is a carboxyl group, a dihydroxybenzyl group, an unsubstituted aryl group having 6 to 18 carbon atoms, or 2-methoxybenzenesulfonamide; and R is a hydrogen atom. In those embodiments, compounds are represented by the following Formula (xi):

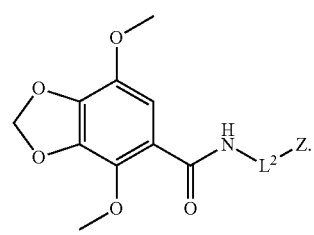

(xi)

In some embodiments of the present invention, compounds are represented by the above Formula (xi), and n1 is 0; $L^2$ is an unsubstituted arylene group having 6 to 18 carbon atoms, and n2 is 1; Z is a hydroxyl group or an unsubstituted ester group having 1 to 6 carbon atoms.

In some embodiments of the present invention, Y is an unsubstituted alkylene group having 1 to 6 carbon atoms or an unsubstituted alkenylene group having 2 to 6 carbon atoms; $L^1$ is an unsubstituted alkylene group having 1 to 6 carbon atoms, and n1 is 1; n2 is 0; Z is an unsubstituted alkyl group having 1 to 6 carbon atoms; and R is a hydrogen atom or an unsubstituted alkyl group having 1 to 6 carbon atoms.

Preferably, the novel compound may be, but is not limited to, any one of the following Compounds 1 to 15:

Compound 1

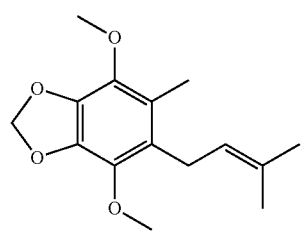 [SMILES: COc1c(C)c(CC=C(C)C)c(OC)c2c1OCO2]

Compound 2

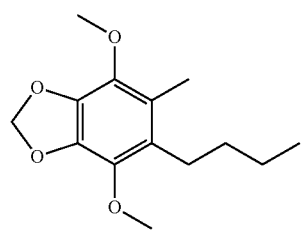 [SMILES: CCCCc1c(C)c(OC)c2c(c1OC)OCO2]

Compound 3

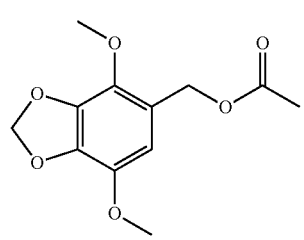

Compound 4

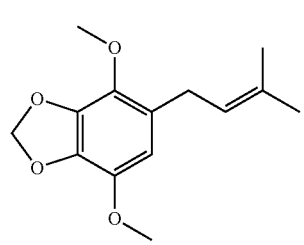 [SMILES: COc1cc(CC=C(C)C)c(OC)c2c1OCO2]

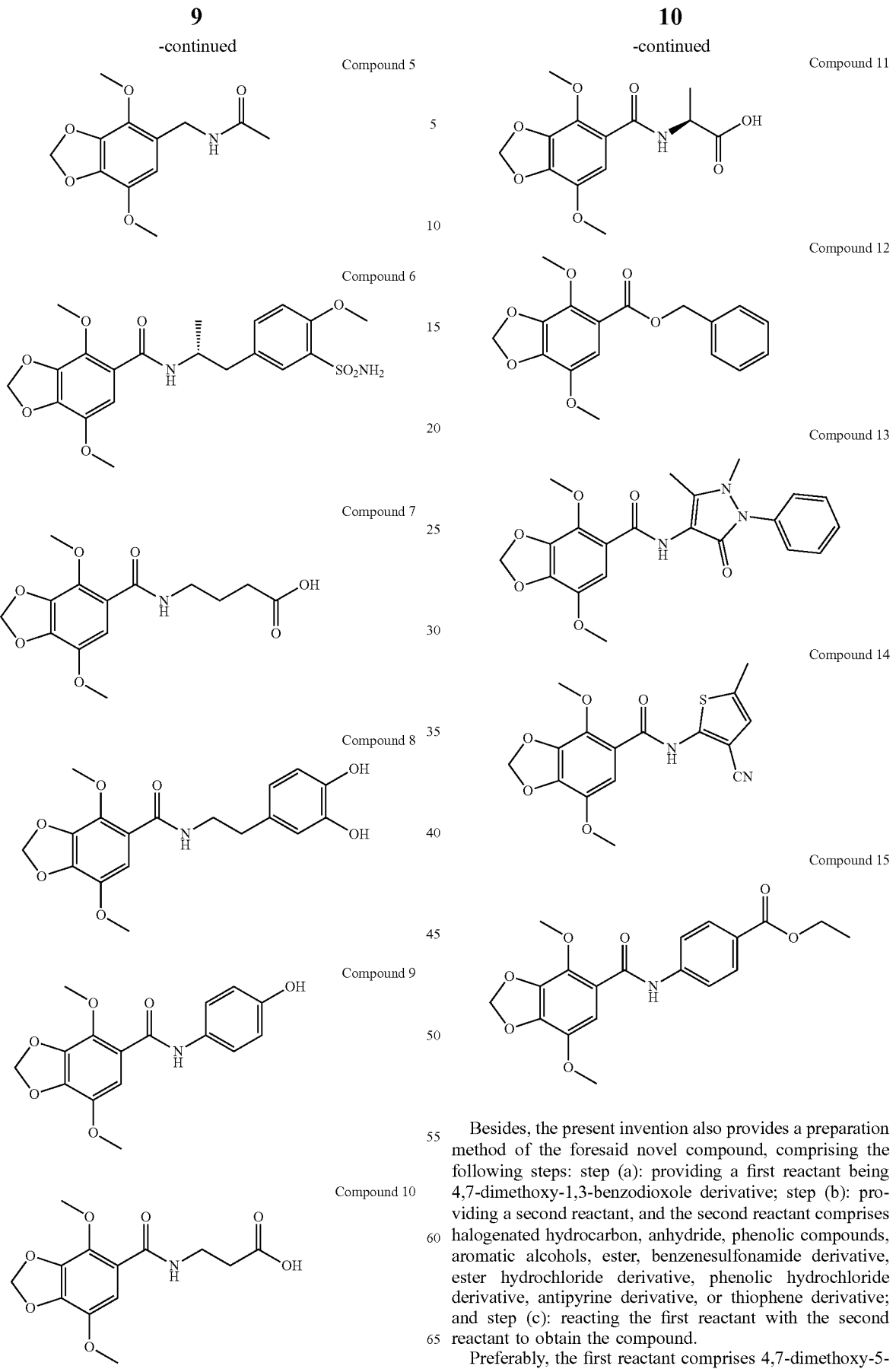

Besides, the present invention also provides a preparation method of the foresaid novel compound, comprising the following steps: step (a): providing a first reactant being 4,7-dimethoxy-1,3-benzodioxole derivative; step (b): providing a second reactant, and the second reactant comprises halogenated hydrocarbon, anhydride, phenolic compounds, aromatic alcohols, ester, benzenesulfonamide derivative, ester hydrochloride derivative, phenolic hydrochloride derivative, antipyrine derivative, or thiophene derivative; and step (c): reacting the first reactant with the second reactant to obtain the compound.

Preferably, the first reactant comprises 4,7-dimethoxy-5-methyl-6-iodo-1,3-benzodioxole, 4,7-dimethoxy-5-iodo-1, 3-benzodioxole, 4,7-dimethoxy-5-hydroxymethyl-1,3-benzodioxole, 4,7-dimethoxy-5-aminomethyl-1,3-benzodioxole, 4,7-dimethoxy-1,3-benzodioxole-5-carboxylic acid, or 4,7-dimethoxy-5-acylchloride-1,3-benzodioxole.

Preferably, the second reactant comprises 3,3-dimethylallyl bromide, 1-bromobutane, acetic anhydride, 4-aminophenol, phenylmethanol, ethyl p-aminobenzoate (also named as benzocaine), 5-[(R)-(2-amino-propyl)]-2-methoxy-benzenesulfonamide, 4-aminobutyric acid methyl ester hydrochloride, β-alanine methyl ester hydrochloride, alanine methyl ester hydrochloride, 4-(2-aminoethyl)-1,2-benzenediol hydrochloride (also named as dopamine hydrochloride), 4-aminoantipyrine, or 2-amino-3-cyano-5-methylthiophene.

In some embodiments of the present invention, the first reactant comprises 4,7-dimethoxy-5-methyl-6-iodo-1,3-benzodioxole, 4,7-dimethoxy-5-iodo-1,3-benzodioxole, 4,7-dimethoxy-5-hydroxymethyl-1,3-benzodioxole, or 4,7-dimethoxy-5-aminomethyl-1,3-benzodioxole; the second reactant comprises halogenated hydrocarbon or anhydride; and the reaction of the first reactant and the second reactant is conducted at −80° C. to 25° C. for 2 hours to 150 hours. Preferably, the second reactant comprises 3,3-dimethylallyl bromide, 1-bromobutane, or acetic anhydride.

In other embodiments of the present invention, the first reactant comprises 4,7-dimethoxy-1,3-benzodioxole-5-carboxylic acid or 4,7-dimethoxy-5-acylchloride-1,3-benzodioxole; the second reactant comprises phenolic compounds, aromatic alcohols, ester, benzenesulfonamide derivative, ester hydrochloride derivative, phenolic hydrochloride derivative, antipyrine derivative, or thiophene derivative; and the reaction of the first reactant and the second reactant is conducted at 0° C. to 60° C. for 0.5 hours to 100 hours. Preferably, the second reactant comprises 4-aminophenol, phenylmethanol, ethyl p-aminobenzoate, 5-[(R)-(2-amino-propyl)]-2-methoxy-benzenesulfonamide, 4-aminobutyric acid methyl ester hydrochloride, β-alanine methyl ester hydrochloride, alanine methyl ester hydrochloride, 4-(2-aminoethyl)-1,2-benzenediol hydrochloride, 4-aminoantipyrine, or 2-amino-3-cyano-5-methylthiophene.

In other embodiments of the present invention, the first reactant is 4,7-dimethoxy-1,3-benzodioxole-5-carboxylic acid; the second reactant comprises aromatic alcohols or antipyrine derivative; and the reaction of the first reactant and the second reactant is conducted at 25° C. to 60° C. for 20 hours to 90 hours. Preferably, the second reactant comprises phenylmethanol or 4-amino antipyrine.

In other embodiments of the present invention, the first reactant is 4,7-dimethoxy-5-acylchloride-1,3-benzodioxole, and the step (a) further comprises a step of subjecting 4,7-dimethoxy-1,3-benzodioxole-5-carboxylic acid by chlorination to form 4,7-dimethoxy-5-acylchloride-1,3-benzodioxole in advance, thereby obtaining the first reactant; the second reactant comprises phenolic compounds, ester, benzenesulfonamide derivative, phenolic hydrochloride derivative, or thiophene derivative; and the reaction of the first reactant and the second reactant is conducted at 0° C. to 60° C. for 0.5 hours to 100 hours. Preferably, the second reactant comprises 4-aminophenol, ethyl p-aminobenzoate, 5-[(R)-(2-amino-propyl)]-2-methoxy-benzenesulfonamide, 4-(2-aminoethyl)-1,2-benzenediol hydrochloride, or 2-amino-3-cyano-5-methylthiophene.

In other embodiments of the present invention, the first reactant is 4,7-dimethoxy-5-acylchloride-1,3-benzodioxole, the second reactant is ester hydrochloride derivative, and the step (c) further comprises steps of reacting the first reactant with the second reactant to obtain a methyl ester intermediate, and then subjecting the methyl ester intermediate to hydrolysis to obtain the compound; wherein, the reaction of the first reactant and the second reactant is conducted at 0° C. to 60° C. for 0.5 hours to 80 hours. Preferably, the second reactant comprises 4-aminobutyric acid methyl ester hydrochloride, β-alanine methyl ester hydrochloride, or alanine methyl ester hydrochloride.

Besides, the present invention also provides a pharmaceutical composition for preventing nerve damage and protecting nerves. The pharmaceutical composition comprises the foresaid novel compound of the present invention and a pharmaceutically acceptable carrier.

Besides, the present invention also provides a use of the foresaid novel compound of the present invention to present nerve damage and protect nerves. Specifically, the use indicates a method for preventing nerve damage and protecting nerve, comprising administration of a therapeutically effective amount of the foresaid novel compound of the present invention.

Preferably, the nerve indicates the brain nervous tissues.

Preferably, said preventing nerve damage and protecting nerves comprises preventing and/or treating stroke and Alzheimer's disease In this specification, said effect of "preventing nerve damage" indicates that when administrating the foresaid novel compound of the present invention in advance, the degree of neuron damage or death can be effectively reduced during nerve damage. Said effect of "protecting nerve" indicates that when administrating the foresaid novel compound of the present invention during nerve damage, the degree of neuron damage or death can be effectively reduced.

In accordance with the present invention, the "pharmaceutically acceptable carrier" or "acceptable carrier" includes pharmaceutically acceptable or food acceptable excipients or additives such as starch, corn starch, gelatin, Arabic gum, food dye, spices, flavoring agent, and preservative. The administration routes include oral, skin, intraperitoneal, intravenous, nasal or eye administration.

In accordance with the present invention, according to patient's age, weight, health condition, type of disease, progress of disease, and affected region, the administration dosage of the aforementioned pharmaceutical composition is determined by related medical personnel depending on the common knowledge in the art. The pharmaceutical composition can be administrated alone or accompanied with other drugs. The administration process should be performed by related medical personnel according to the routine method in pharmacy.

In this specification, a range represented by "a lower-endpoint value to an upper-endpoint value", if not particularly specified, indicates that the range is more than or equal to the lower-endpoint value and less than or equal to the upper-endpoint value. For example, temperature −80° C. to 25° C. indicates that the range of temperature is "more than or equal to −80° C. and less than or equal to 25° C.".

Other objectives, advantages, and novel features of the invention will become more apparent from the following detailed description when taken in conjunction with the accompanying drawings.

DETAILED DESCRIPTION OF THE PREFERRED EMBODIMENTS

Figure 1:
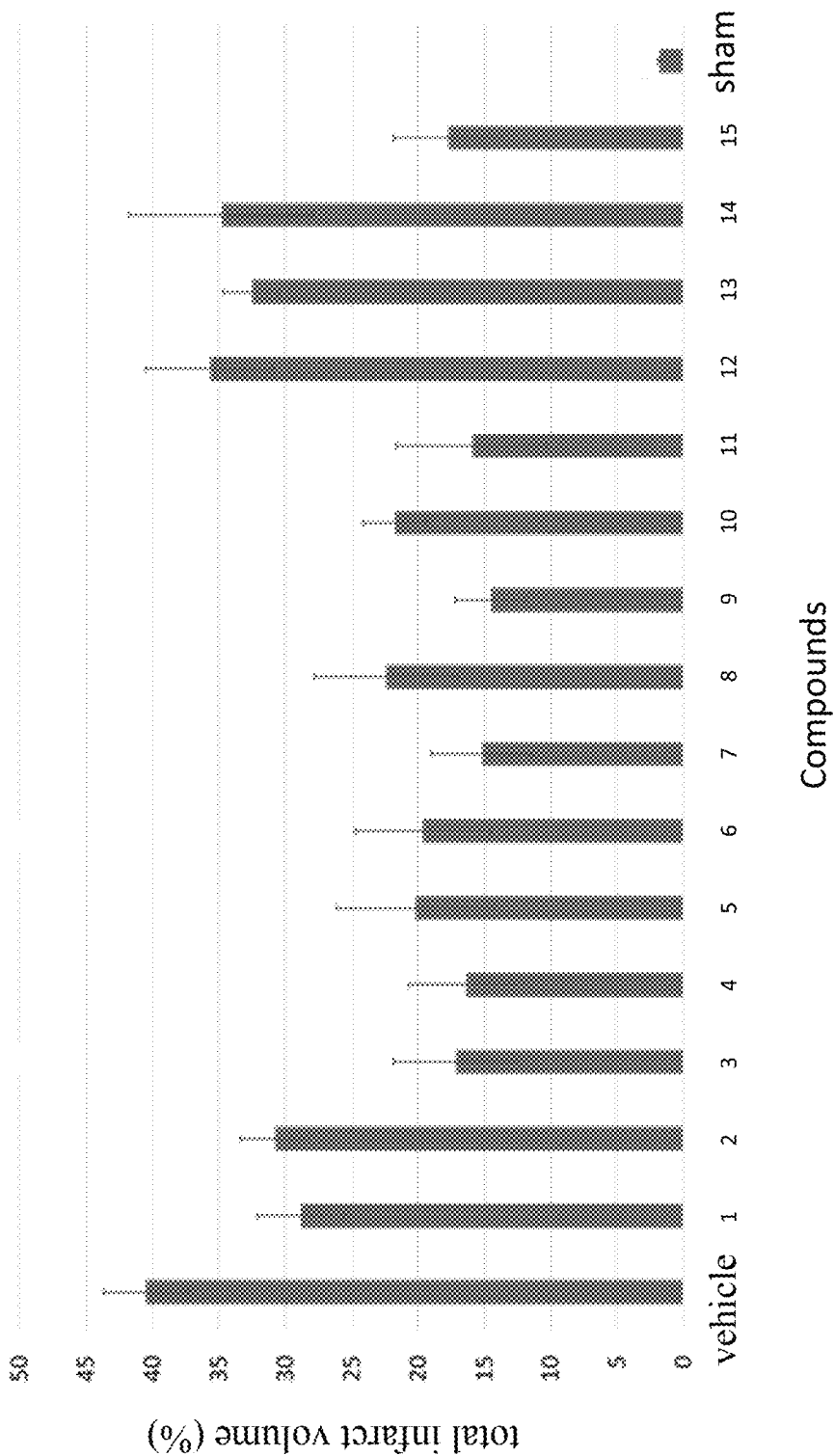
FIG. 1 is the effect of preventing nerve damage after the rats were administrated with the compounds of Examples 1 to 15.

Several Examples are provided below to illustrate the implementation of the present invention. A person skilled in the art can easily realize the advantages and effects of the present invention in accordance with the contents of the specification. Various modifications and variations could be made in order to practice or apply the present invention without departing from the spirit and scope of the invention.

Example 1

0.65 grams (g) of 4,7-dimethoxy-5-methyl-6-iodo-1,3-benzodioxole and 3 milliliters (ml) of tetrahydrofuran were added into a 100 ml three-neck round bottom flask, and the temperature was cooled down to around −80° C. under nitrogen. Then, 1.5 ml of n-butyllithium solution (1.6 molarity (M)) was slowly added, and subsequently a mixture of 3,3-dimethylallyl bromide (0.35 ml) in tetrahydrofuran (2 ml). The reaction mixture was stirred for 70 hours. After the reaction was completed, 5 ml of water and 5 ml of ethyl acetate (EA) were added for extraction. The EA layer (i.e., EA phase) was separated and washed two times with water. The EA layer was dried over sodium sulfate and then filtered. The filtered solid was rinsed three times with EA. The three EA filtrates were combined with the foresaid EA solution and the solvent was removed by a rotary evaporator. The crude product was purified by column chromatography (silica gel: 80 g; filled length of the column: 15 cm; and the eluent being 100% heptane), and 0.22 g of a yellow liquid was obtained with HPLC purity 97.1% (area percent) as the compound of Example 1.

The structure of the compound of Example 1 was identified by nuclear magnetic resonance (NMR) and Mass and shown in Table 1. The results of NMR and Mass were as follows: $^1$H-NMR (500 MHz, CDCl$_3$): δ=5.892 (s, 2H), 5.015 (t, 1H), 3.868 (s, 6H), 3.279 (d, 2H), 2.108 (s, 3H), 1.760 (s, 3H), 1.677 (s, 3H). Mass spectrometry: [M-C$_4$H$_7$]$^+$; C$_{11}$H$_{13}$O$_4$; 209.18.

Example 2

3.24 g of 4,7-dimethoxy-5-methyl-6-iodo-1,3-benzodioxole and 25 ml of tetrahydrofuran were added into a 100 ml three-neck round bottom flask, and the temperature was cooled down to around −80° C. under nitrogen. Then, 7 ml of n-butyllithium solution (1.6 M) was slowly added, and then 2.2 ml of 1-bromobutane. The reaction mixture was stirred for 3 hours. After the reaction was completed, the temperature was warmed up to room temperature, and 25 ml of water and 25 ml of EA were added for extraction. The organic layer was separated and washed with 30 ml of water each for two times. The organic layer was dried over sodium sulfate and then filtered. The filtered solid was rinsed three times with EA. The three EA filtrates was combined with the foresaid organic solution and the solvent was removed by a rotary evaporator. The crude product was purified by column chromatography (silica gel: 60 g; filled length of the column: 12 cm; and the eluent being 100% heptane), and 0.9 g product was obtained with HPLC purity 96.8% (area percent) as the compound of Example 2.

The structure of the compound of Example 2 was identified by NMR and Mass and shown in Table 1. The results of NMR and Mass were as follows: $^1$H-NMR (500 MHz, CDCl$_3$): δ=5.887 (s, 2H), 3.886 (s, 3H), 3.870 (s, 3H), 2.548 (t, 2H), 2.119 (s, 3H), 1.409-1.379 (m, 4H), 0.935 (t, 3H). Mass spectrometry: [M+H]$^+$; C$_{14}$H$_{21}$O$_4$; 253.21.

Example 3

0.24 g of 4,7-dimethoxy-5-hydroxymethyl-1,3-benzodioxole, 3 ml of tetrahydrofuran and 3 ml of triethylamine were added into a 100 ml three-neck round bottom flask and cooled in an ice bath. After adding 0.45 ml of acetic anhydride, the temperature was warmed up to room temperature. The reaction mixture was stirred for 144 hours. After the reaction was completed, the solvent was removed by a rotary evaporator, and 10 ml of dichloromethane was added to dissolve the residue. The dichloromethane solution was washed first with 10 ml of saturated sodium bicarbonate solution and then with 10 ml water. The organic layer was dried over sodium sulfate, filtered and evaporated to yield 0.29 g of an off-white powder with 92.6% (area percent) HPLC purity as the compound of Example 3.

The structure of the compound of Example 3 was identified by NMR and Mass and shown in Table 1. The results of NMR and Mass were as follows: $^1$H-NMR (500 MHz, CDCl$_3$): δ=6.520 (s, 1H), 5.980 (s, 2H), 5.049 (s, 2H), 3.923 (s, 3H), 3.861 (s, 3H), 2.078 (s, 3H). Mass spectrometry: [M-C$_2$H$_3$O$_2$]$^+$; C$_{10}$H$_{11}$O$_4$; 195.14.

Example 4

0.57 g of 4,7-dimethoxy-5-iodo-1,3-benzodioxole and 4 ml of tetrahydrofuran were added into a 100 ml three-neck round bottom flask, and the temperature was cooled down to around −80° C. under nitrogen. After adding 1.5 ml of 1.6M n-butyllithium solution, a mixture of 3,3-dimethylallyl bromide (0.35 ml) in tetrahydrofuran (3 ml) was added. The reaction mixture was stirred for 2.5 hours. After the reaction was completed, the temperature was warmed up to 0° C., and 10 ml of water and 10 ml of EA were added. The EA layer was separated and washed again with 10 ml of water. The EA solution was dried over sodium sulfate, filtered and evaporated to yield 0.44 g of a deep brown liquid. The liquid was purified by column chromatography (silica gel: 29.1 g; filled length of the column: 6 cm; and the eluent being EA:heptane=1:50) to obtain 66.3 milligrams (mg) solid with 96.5% (area percent) of HPLC purity as the compound of Example 4.

The structure of the compound of Example 4 was identified by NMR and Mass and shown in Table 1. The results of NMR and Mass were as follows: $^1$H-NMR (500 MHz, CDCl$_3$): δ=6.297 (s, 1H), 5.935 (s, 2H), 5.229 (t, 1H), 3.871 (s, 3H), 3.850 (s, 3H), 3.244 (d, 2H), 1.729 (s, 3H), 1.716 (s, 3H). Mass spectrometry: [M-C$_4$H$_7$]$^+$; C$_{10}$H$_{11}$O$_4$; 195.15.

Example 5

After 1.0 g of 4,7-dimethoxy-5-aminomethyl-1,3-benzodioxole was placed into a 100 ml three-neck round bottom flask under nitrogen, 10 ml of tetrahydrofuran and 1.5 ml of triethylamine were added, and then cooled in an ice bath. Next, 0.5 ml of acetic anhydride was added and stirred for 17 hours. After the reaction was completed, 10 ml of methanol was added and the solvent was removed by a rotary evaporator, and then 30 ml of dichloromethane was added to dissolve the residue. The dichloromethane layer was washed with 30 ml saturated sodium bicarbonate solution and subsequently 30 ml water and 30 ml saline, and then separated. The dichloromethane solution was dried over sodium sulfate, filtered and evaporated to yield 1.16 g of a light yellow powder. Afterward, the powder was purified by column chromatography (silica gel: 50.1 g; filled length of the column: 11 cm; and the eluent being EA:heptane=1:10 to 2:1), and the product was collected and the solvent thereof was removed by the rotary evaporator to obtain 0.94 g of the compound of Example 5 with 89.6% (area percent) of HPLC purity.

The structure of the compound of Example 5 was identified by NMR and Mass and shown in Table 1. The results of NMR and Mass were as follows: $^1$H-NMR (500 MHz, CDCl$_3$): δ=6.479 (s, 1H), 5.959 (s, 2H), 5.890 (br, 1H, NH), 4.324 (d, 2H), 3.942 (s, 3H), 3.843 (s, 3H), 1.969 (s, 3H). Mass spectrometry: [M+H]$^+$; C$_{12}$H$_{16}$NO$_5$; 254.23, [M+Na]$^+$; 276.16.

Example 6

0.51 g of 4,7-dimethoxy-1,3-benzodioxole-5-carboxylic acid, 1.3 ml of dichloromethane and 2 droplets of dimethylformamide were added into a 100 ml three-neck round bottom flask, and then 0.34 ml of oxalyl chloride was added to conduct chlorination at room temperature for 2 hours. Afterward, the redundant oxalyl chloride and the solvent were removed to obtain an acyl chloride. The acyl chloride was transferred to a 100 ml single-neck round bottom flask, and diluted with 5 ml of dichloromethane and 2.5 ml of dichloromethane solution, which comprised 0.51 g of 5-[(R)-(2-amino-propyl)]-2-methoxy-benzenesulfonamide, and then 1.3 ml of triethylamine were added and stirred for 19.5 hours at room temperature. After the reaction was completed, 10 ml of water and 10 ml of EA were added for extraction, and the organic layer was separated. The solvent of the organic layer was removed by a rotary evaporator to obtain 0.9 g of an off-white needle-like solid. The solid was stirred with 17.5 ml of heptane, and filtered to obtain 0.59 g of a white powder as the compound of Example 6 with 96.5% (area percent) of HPLC purity.

The structure of the compound of Example 6 was identified by NMR and Mass and shown in Table 1. The results of NMR and Mass were as follows: $^1$H-NMR (500 MHz, CDCl$_3$): δ=7.789 (d, 1H, NH), 7.742 (s, 1H), 7.438 (d, 1H), 7.387 (s, 1H), 6.985 (d, 1H), 6.045 (s, 2H), 5.095 (s, 2H, NH$_2$), 4.396 (m, 1H), 3.983 (s, 3H), 3.933 (s, 3H), 3.885 (s, 3H), 2.921-2.789 (m, 2H), 1.215 (d, 3H). Mass spectrometry: [M+H]$^+$; C$_{20}$H$_{25}$N$_2$O$_8$S; 453.30, [M+Na]$^+$; 475.26.

Example 7

1.14 g of 4,7-dimethoxy-1,3-benzodioxole-5-carboxylic acid, 2 ml of toluene and 2 droplets of dimethylformamide were added into a 500 ml single-neck round bottom flask, and then 0.75 ml of thionyl chloride was added and heated to 60° C. to conduct reaction for 1.5 hours. After the reaction was completed, the solvent was removed by a rotary evaporator, and the residue was dissolved in 20 ml of tetrahydrofuran, and evaporated again to obtain an acyl chloride. Next, the acyl chloride was mixed with 20 ml of tetrahydrofuran, and the temperature was cooled down to 0° C., and then 0.81 g of 4-aminobutyric acid methyl ester hydrochloride and 3 ml of triethylamine were added, and stirred for 19 hours at room temperature. After the reaction was completed, 20 ml of water and 20 ml of EA were added for extraction, and the organic layer was separated and saved. The water layer was extracted again with another 20 ml of EA and the EA layer was combined with the EA solution saved before. The EA solution was dried over sodium sulfate, filtered and evaporated to obtain 1.4 g of methyl ester intermediate (yellow liquid) with 86.3% (area percent) of HPLC purity.

Next, 0.80 g of the methyl ester intermediate, 8 ml of tetrahydrofuran and 8 ml of methanol were added into a 100 ml double-neck round bottom flask, and the temperature was cooled down to 0° C. Then, 8 ml of lithium hydroxide solution, which comprised 0.37 g of lithium hydroxide, was added and the reaction mixture was stirred for 67 hours at room temperature. After the reaction was completed, the temperature was cooled down to 0° C., and 25 ml of EA was added, and the pH was adjusted to 3.28 by 1M hydrochloric acid solution. Then, the temperature was warmed up to room temperature and the upper organic layer was separated and saved. The lower water layer solution was extracted with 25 ml of EA. The EA layer was separated and combined with the pre-saved EA solution. The combined EA solution was dried over sodium sulfate, filtered and evaporated to yield 0.75 g of a yellow needle-like solid as the compound of Example 7 with 95.5% (area percent) of HPLC purity.

The structure of the compound of Example 7 was identified by NMR and Mass and shown in Table 1. The results of NMR and Mass were as follows: $^1$H-NMR (500 MHz, CDCl$_3$): δ=8.074 (br, 1H, NH), 7.431 (s, 1H), 6.060 (s, 2H), 4.024 (s, 3H), 3.899 (s, 3H), 3.530 (m, 2H), 2.450 (t, 2H), 1.953 (m, 2H). Mass spectrometry: [M+H]$^+$; C$_{14}$H$_{18}$NO$_7$; 312.16, [M+Na]$^+$; 334.18.

Example 8

0.68 g of 4,7-dimethoxy-1,3-benzodioxole-5-carboxylic acid, 20 ml of toluene and 5 droplets of dimethylformamide were added into a 500 ml single-neck round bottom flask, and then 0.55 ml of thionyl chloride was added and heated to 60° C. to conduct reaction for 1 hour. After the reaction was completed, the redundant thionyl chloride and the solvent were removed by a rotary evaporator, and the residue was dissolved in 20 ml of tetrahydrofuran, and evaporated again to obtain an acyl chloride. Next, the acyl chloride was mixed with 20 ml of tetrahydrofuran, and the temperature was cooled down to 0° C., and then 10.9 ml of dopamine hydrochloride solution, which comprised 0.57 g of dopamine hydrochloride and 0.9 ml of trimethylamine in 10 ml of tetrahydrofuran, was added and reacted for 46 hours at room temperature. After the reaction was completed, 20 ml of water and 20 ml of EA were added for extraction, and the upper layer (EA solution) was separated and saved. The lower water layer was further extracted with another 20 ml of EA. The EA layer was separated and combined with the pre-saved EA solution. The combined EA solution was washed with 10 ml 0.1M hydrochloric acid solution, and subsequently 10 ml water and 10 ml saline, and then separated. The EA solution was dried over sodium sulfate, filtered and evaporated to yield 1.05 g of a crude product. Afterward, the crude product was purified by column chromatography (silica gel: 30 g; filled length of the column: 6 cm; and the eluent being EA:heptane=1:10 to 5:1) to obtain 0.65 g of a major product. Afterward, the major product was purified by reverse column chromatography (C-18 silica gel: 28.3 g; the filled length of the column: 4.5 cm; and the eluent being acetonitrile:water=1:1) to obtain 0.22 g of the compound of Example 8 with 98.8% (area percent) of HPLC purity.

The structure of the compound of Example 8 was identified by NMR and Mass and shown in Table 1. The results of NMR and Mass were as follows: $^1$H-NMR (500 MHz, DMSO-d$_6$): δ=8.735 (s, 1H, OH), 8.641 (s, 1H, OH), 7.999 (t, 1H, NH), 7.051 (s, 1H), 6.645 (d, 1H), 6.614 (s, 1H), 6.469 (d, 1H), 6.071 (s, 2H), 3.780 (s, 3H), 3.768 (s, 3H), 3.424 (m, 2H), 2.627 (t, 2H). Mass spectrometry: [M+H]$^+$; $C_{18}H_{20}NO_7$; 362.28, [M+Na]$^+$; 384.27.

Example 9

1.13 g of 4,7-dimethoxy-1,3-benzodioxole-5-carboxylic acid, 20 ml of toluene and 2 droplets of dimethylformamide were added into a 500 ml single-neck round bottom flask, and then 0.8 ml of thionyl chloride was added and heated to 60° C. to conduct reaction for 1 hour. Then, the redundant thionyl chloride and the solvent were removed by a rotary evaporator, and the residue was dissolved in 20 ml of tetrahydrofuran, and evaporated again to obtain an acyl chloride. Next, the acyl chloride was dissolved in 20 ml of tetrahydrofuran, and cooled in an ice-bath, and then 0.55 g of 4-aminophenol and 1.4 ml of triethylamine were added, after 30 minutes, the reaction mixture was warmed up to room temperature and reacted for 22 hours. After the reaction was completed, 20 ml of water was added, and the upper organic layer was separated and saved. The lower water layer solution was extracted again with another 20 ml of EA. The EA layer was separated and combined with the pre-saved organic solution. The combined solution was washed with 20 ml of water, and subsequently 20 ml of saline, and then separated. The combined solution was dried over sodium sulfate, filtered and evaporated to obtain 1.62 g of a crude product. Afterward, the crude product was purified by column chromatography (silica gel: 39.9 g; filled length of the column: 8 cm; and the eluent being EA:heptane=1:10 to 5:1) to yield 1.08 g of the compound of Example 9 with 96.0% (area percent) of HPLC purity.

The structure of the compound of Example 9 was identified by NMR and Mass and shown in Table 1. The results of NMR and Mass were as follows: $^1$H-NMR (500 MHz, DMSO-d$_6$): δ=9.790 (s, 1H, OH), 9.220 (s, 1H, NH), 7.468 (d, 2H), 6.961 (s, 1H), 6.710 (d, 2H), 6.095 (s, 2H), 3.915 (s, 3H), 3.809 (s, 3H). Mass spectrometry: [M+H]$^+$; $C_{16}H_{16}NO_6$; 318.15, [M+Na]$^+$; 340.15.

Example 10

0.57 g of 4,7-dimethoxy-1,3-benzodioxole-5-carboxylic acid, 15 ml of toluene and 3 droplets of dimethylformamide were added into a 250 ml single-neck round bottom flask, and then 0.4 ml of thionyl chloride was added and heated to 60° C. to conduct reaction for 1 hour. After the reaction was completed, the redundant thionyl chloride and the solvent were removed by a rotary evaporator, and the residue was dissolved in 15 ml of 2-methyl tetrahydrofuran, and evaporated again to obtain an acyl chloride. Next, the acyl chloride was dissolved with 15 ml of tetrahydrofuran, and cooled in an ice-bath, and then 0.51 g of β-alanine methyl ester hydrochloride and 1.4 ml of triethylamine were added, after 30 minutes, the reaction mixture was warmed up to room temperature and reacted for 71 hours. After the reaction was completed, 20 ml of water and 20 ml of EA were added to perform the extraction. The upper organic layer was separated and further washed with 20 ml of water, and then 20 ml of saline. The separated organic layer was dried over sodium sulfate, filtered and evaporated to get 0.56 g of a yellow solid. Afterward, the yellow solid were purified by column chromatography (silica gel: 31 g; filled length of the column: 6 cm; and the eluent being EA:heptane=1:10 to 1:2) to yield 0.41 g of methyl ester intermediate with 99.3% (area percent) of HPLC purity.

Next, 0.38 g of the methyl ester intermediate, 4 ml of tetrahydrofuran and 4 ml of methanol were added into a 250 ml single-neck round bottom flask and cooled in an ice bath. Then, 4 ml of lithium hydroxide solution, which comprised 0.19 g of lithium hydroxide, was slowly added to react at room temperature for 79 hours. After the reaction was completed, the organic solvent was removed by the rotary evaporator, and 20 ml of dichloromethane was added in the residue solution. After cooling in an ice-bath, the pH value was adjusted to 1.75 by 1M hydrochloric acid solution, and the temperature was warmed up to room temperature and the organic layer (dichloromethane solution) was separated and saved. The water layer was extracted with 40 ml each of EA twice. The EA layers were combined with the pre-saved dichloromethane solution. After the combined organic solution was washed with 40 ml each of water twice, the organic solution was dried over sodium sulfate, filtered and evaporated to get 0.35 g of a white solid as the compound of Example 10 with 96.1% (area percent) of HPLC purity.

The structure of the compound of Example 10 was identified by NMR and Mass and shown in Table 1. The results of NMR and Mass were as follows: $^1$H-NMR (500 MHz, CD$_3$OD): δ=7.255 (s, 1H), 6.057 (s, 2H), 3.997 (s, 3H), 3.858 (s, 3H), 3.633 (m, 2H), 2.608 (t, 2H). Mass spectrometry: [M+H]$^+$; $C_{13}H_{16}NO_7$; 298.15, [M+Na]$^+$; 320.13.

Example 11

1.14 g of 4,7-dimethoxy-1,3-benzodioxole-5-carboxylic acid, 20 ml of toluene and 2 droplets of dimethylformamide were added into a 250 ml single-neck round bottom flask, and then 0.8 ml of thionyl chloride was added and heated to 60° C. to conduct reaction for 1 hour. After the reaction was completed, the redundant thionyl chloride and the solvent were removed by a rotary evaporator, and the residue was dissolved in 20 ml of 2-methyl tetrahydrofuran, and evaporated again to obtain an acyl chloride. Next, the acyl chloride was dissolved in 20 ml of tetrahydrofuran, and cooled in an ice-bath, and then 0.94 g of alanine methyl ester hydrochloride and 3 ml of triethylamine were added, after 30 minutes, the reaction mixture was warmed up to room temperature and reacted for 72 hours. After the reaction was completed, 20 ml of water and 20 ml of EA were added, and the upper organic layer was separated. The upper organic layer was further washed with 20 ml of water, and then 20 ml of saline. The organic layer was dried over sodium sulfate, filtered and evaporated to obtain a yellow liquid with wet weight of 1.27 g. Afterward, the yellow liquid was purified by column chromatography (silica gel: 31 g; filled length of the column: 6 cm; and the eluent being EA:heptane=1:10 to 1:2) to yield 1.02 g of methyl ester intermediate with 97.1% (area percent) of HPLC purity.

Next, 1.02 g of the methyl ester intermediate, 10 ml of tetrahydrofuran and 10 ml of methanol were added into a 250 ml single-neck round bottom flask, and cooled in an ice-bath. Then, 10 ml of lithium hydroxide solution, which comprised 0.44 g of lithium hydroxide, was slowly added, and reacted at room temperature for 24 hours. After the reaction was completed, the organic solvent was removed by a rotary evaporator, and 20 ml of dichloromethane was added to the residue solution and cooled in an ice-bath. Then, the pH was adjusted to 4.6 by 1M hydrochloric acid solution. After addition, the temperature was warm up to room temperature. The lower dichloromethane layer was separated and saved. The upper water layer was extracted with 20 ml of EA and then the EA layer was separated. The EA layer was combined with the pre-saved dichloromethane solution. Then, the solvent was removed by a rotary evaporator to obtain 0.97 g of an off-white powder. Next, the off-white powder was dissolved in 20 ml of EA, and washed with 20 ml of water, and then with 20 ml of saline. The organic solution was evaporated to obtain 0.75 g of an off-white powder as the compound of Example 11 with 98.2% (area percent) of HPLC purity.

The structure of the compound of Example 11 was identified by NMR and Mass and shown in Table 1. The results of NMR and Mass were as follows: $^1$H-NMR (500 MHz, DMSO-d$_6$): δ=12.8 (br, 1H, COOH), 8.446 (d, 1H, NH), 7.102 (s, 1H), 6.110 (s, 2H), 4.416 (m, 1H), 3.911 (s, 3H), 3.795 (s, 3H), 1.374 (d, 3H). Mass spectrometry: [M+H]$^+$; C$_{13}$H$_{16}$NO$_7$; 298.15, [M+Na]$^+$; 320.13.

Example 12

1.13 g of 4,7-dimethoxy-1,3-benzodioxole-5-carboxylic acid, 5.5 ml of benzyl alcohol and 3 droplets of concentrated sulfuric acid were added into a 250 ml double-neck round bottom flask, and then heated to 60° C. to react for 28 hours. After the reaction was completed, 50 ml of water was added and the lower layer was separated and evaporated to obtain a deep brown liquid. Then, the deep brown liquid was purified by column chromatography (silica gel: 45 g; filled length of the column: 9 cm; and the eluent being EA:heptane=1:20 to 1:10) to obtain a transparent liquid with wet weight of 1.87 g. Then, the transparent liquid was dried under vacuum to obtain 1.35 g of a white powder as the compound of Example 12 with 98.4% (area percent) of HPLC purity.

The structure of the compound of Example 12 was identified by NMR and Mass and shown in Table 1. The results of NMR and Mass were as follows: $^1$H-NMR (500 MHz, CDCl$_3$): δ=7.461-7.329 (m, 5H), 7.110 (s, 1H), 6.054 (s, 2H), 5.343 (s, 2H), 3.897 (s, 3H), 3.873 (s, 3H). Mass spectrometry: [M+H]$^+$; C$_{17}$H$_{17}$O$_6$; 317.14, [M+Na]$^+$; 339.13.

Example 13

0.57 g of 4,7-dimethoxy-1,3-benzodioxole-5-carboxylic acid, 0.51 g of 4-aminoantipyrine, 10 ml of tetrahydrofuran and 5 ml of water were added into a 100 ml double-necked flask, and then 0.8 g of 1-ethyl-3-(3-dimethylaminopropyl) carbodiimide was added to conduct reaction at room temperature for 74 hours. After the reaction was completed, tetrahydrofuran was removed by a rotary evaporator, and the residue solution was extracted with 20 ml of EA. Then, the EA solution was washed with 20 ml of water each for three times, and then dried over sodium sulfate, filtered and evaporated to obtain 0.8 g of a deep orange liquid as the compound of Example 13 with 97.6% (area percent) of HPLC purity.

The structure of the compound of Example 13 was identified by NMR and Mass and shown in Table 1. The results of NMR and Mass were as follows: $^1$H-NMR (500 MHz, CDCl$_3$): δ=9.445 (s, 1H, NH), 7.475-7.419 (m, 5H), 7.302-7.274 (m, 1H), 6.078 (s, 2H), 4.125 (s, 3H), 3.914 (s, 3H), 3.039 (s, 3H), 2.387 (s, 3H). Mass spectrometry: [M+H]$^+$; C$_{21}$H$_{22}$N$_3$O$_6$; 412.34, [M+Na]$^+$; 434.32.

Example 14

0.57 g of 4,7-dimethoxy-1,3-benzodioxole-5-carboxylic acid, 10 ml of toluene and 1 droplet of dimethylformamide were added into a 100 ml single-necked flask, and then 0.4 ml of thionyl chloride was added and heated to 60° C. to conduct reaction for 1.5 hours. After the reaction was completed, the redundant thionyl chloride and the solvent were removed by a rotary evaporator, and the residue was dissolved in 10 ml of 2-methyl tetrahydrofuran, and evaporated again to obtain an acyl chloride. Afterward, 10 ml of 2-methyl tetrahydrofuran was added to the acyl chloride and cooled in an ice-bath, then 0.35 g of 2-amino-3-cyano-5-methylthiophene and 1.8 ml of triethylamine were added, and reacted at room temperature for 96 hours. After the reaction was completed, 10 ml of water and 10 ml of EA were added. The aqueous layer was separated and further washed with 20 ml each of EA for three times. Then, 20 ml each of dichloromethane was added to the aqueous layer to conduct the extraction for three times. The combined dichloromethane solution was dried over sodium sulfate, filtered and evaporated to obtain 0.47 g of a yellow powder as the compound of Example 14 with 90.82% (area percent) of HPLC purity.

The structure of the compound of Example 14 was identified by NMR and Mass and shown in Table 1. The results of NMR and Mass were as follows: $^1$H-NMR (500 MHz, CDCl$_3$): δ=11.420 (s, 1H, NH), 7.517 (s, 1H), 6.640 (s, 1H), 6.110 (s, 2H), 4.267 (s, 3H), 3.904 (s, 3H), 2.416 (s, 3H). Mass spectrometry: [M+H]$^+$; C$_{16}$H$_{15}$N$_2$O$_5$S; 347.14, [M+Na]$^+$; 369.15.

Example 15

0.57 g of 4,7-dimethoxy-1,3-benzodioxole-5-carboxylic acid, 10 ml of toluene and 1 droplet of dimethylformamide were added into a 250 ml single-neck round bottom flask, and then 0.42 ml of thionyl chloride was added and heated to 60° C. to conduct reaction for 1.5 hours. After the reaction was completed, the redundant thionyl chloride and the solvent were removed by a rotary evaporator, and the residue was dissolved in 10 ml of 2-methyl tetrahydrofuran, and evaporated again to obtain an acyl chloride. Afterward, 10 ml of 2-methyl tetrahydrofuran was added, and then the temperature was cooled down to 0° C. Next, 0.42 g of benzocaine and 0.8 ml of triethylamine were added, and reacted at room temperature for 22 hours. After the reaction was completed, 10 ml of water was added, and then extracted first with 10 ml each of EA for three times, and then with 10 ml each of dichloromethane for three times. The combined EA and dichloromethane layers were dried over sodium sulfate, filtered and then evaporated to obtain an off-white powder with wet weight of 0.98 g. Next, the off-white powder was dissolved in 50 ml of dichloromethane, and washed with 25 ml each of water for three times, and then dried with sodium sulfate, filtered and evaporated to obtain 0.92 g of an off-white powder as the compound of Example 15 with 93.0% (area percent) of HPLC purity.

The structure of the compound of Example 15 was identified by NMR and Mass and shown in Table 1. The results of NMR and Mass were as follows: $^1$H-NMR (500 MHz, CDCl$_3$): δ=10.074 (s, 1H, NH), 8.044 (d, 2H), 7.727 (d, 2H), 7.515 (s, 1H), 6.109 (s, 2H), 4.371 (q, 2H), 4.131 (s, 3H), 3.931 (s, 3H), 1.398 (t, 3H). Mass spectrometry: [M+H]⁺; C$_{19}$H$_{20}$NO$_7$; 347.30, [M+Na]⁺; 396.35.
TABLE 1
The structures of compounds of Examples 1 to 15.
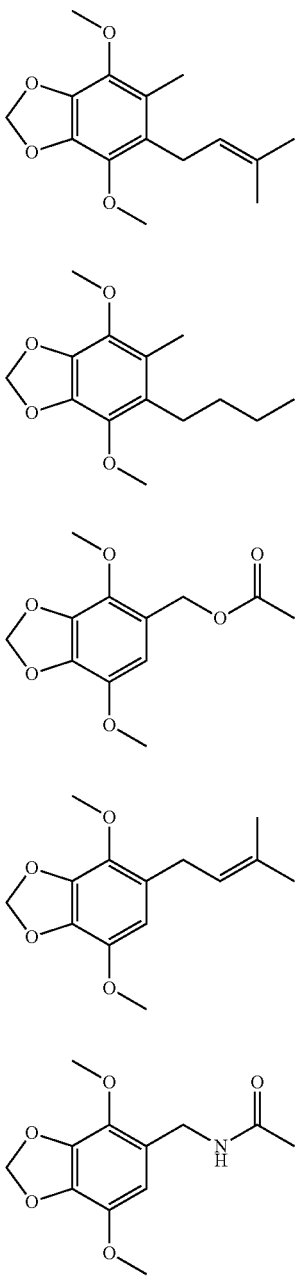
Example 1
Example 2
Example 3
Example 4
Example 5
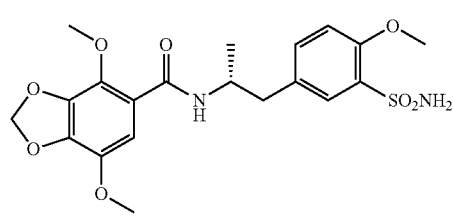 [SMILES: COc1ccc(C[C@@H](C)NC(=O)c2cc(OC)c3c(c2OC)OCO3)cc1S(N)(=O)=O]
Example 6
TABLE 1-continued
The structures of compounds of Examples 1 to 15.
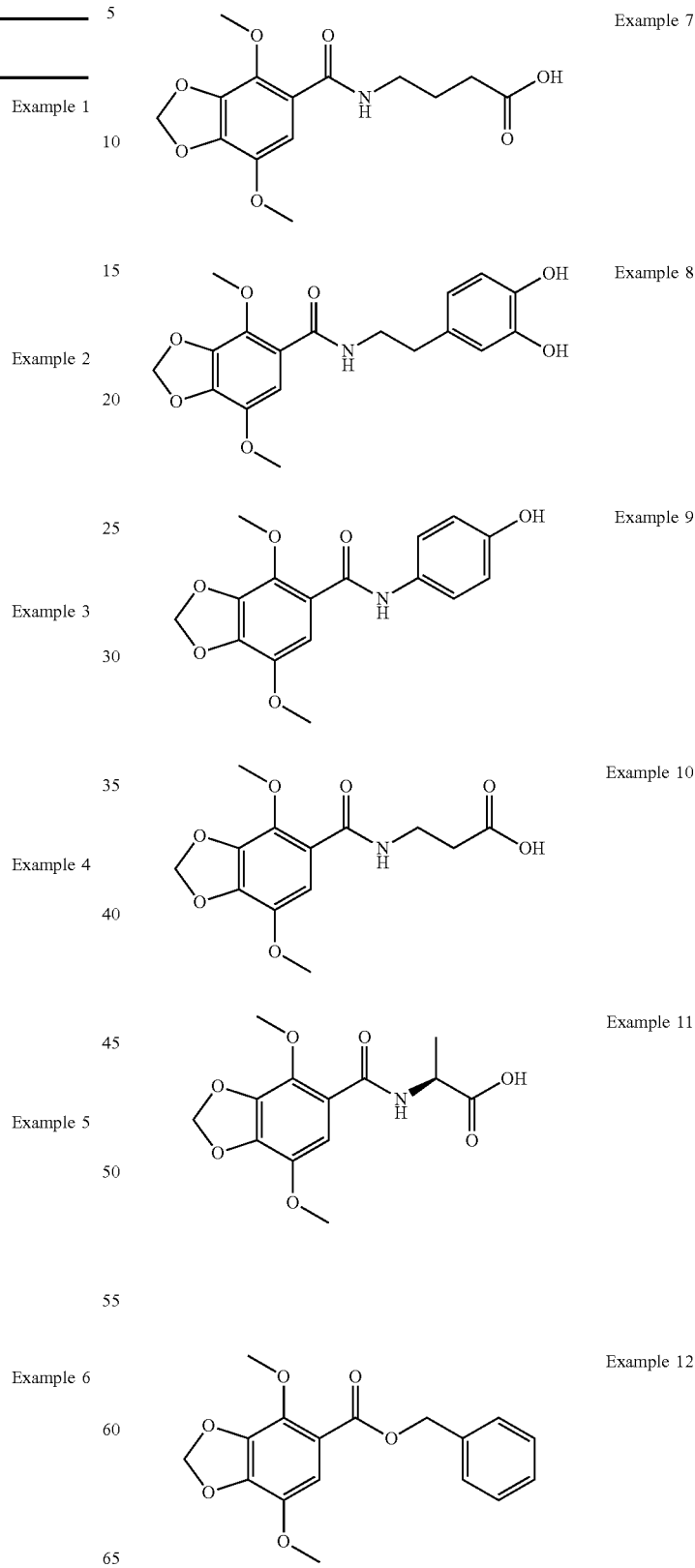
Example 7
Example 8
Example 9
Example 10
Example 11
Example 12

TABLE 1-continued

The structures of compounds of Examples 1 to 15.

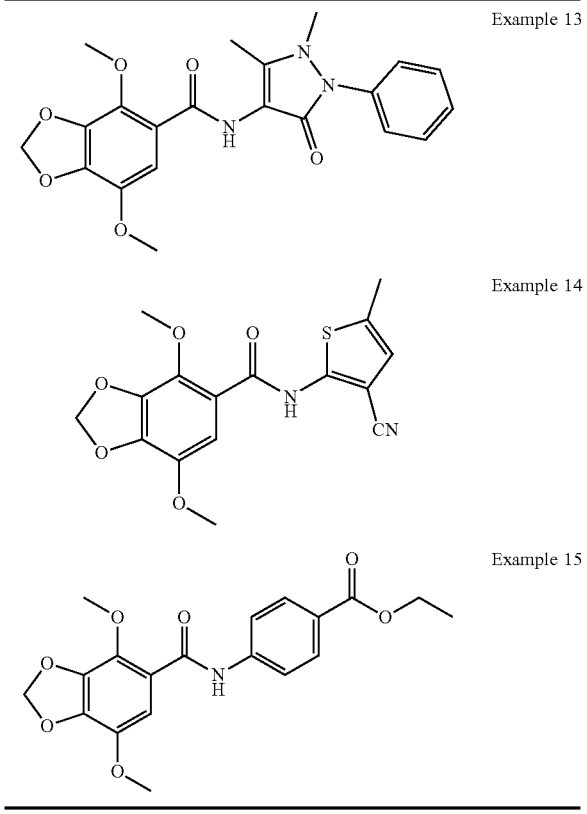

Example 13

Example 14

Example 15

Test Example 1: Evaluation of the Effect of Preventing Nerve Damage

The compounds of Examples 1 to 15 were adopted and dissolved in a specific solvent to obtain the test samples (concentration: 10 mg/ml). The specific solvent was made of dimethyl sulfoxide (DMSO), cremophor EL (CrEL) and water, with the relative volume ratio of 10:20:70, respectively. Besides the foresaid experimental groups, only pure solvent used was treated as vehicle group, and a sham group, which was not administrated with any compound or solvent or with nylon monofilament to cause obstruction and ischemia, was also included.

In this test example, transient focal Middle Cerebral Artery Occlusion/Reperfusion model (MCAO/R model) was adopted to simulate ischemic stroke for evaluating the subsequent nerve damage. Specifically, male Sprague Dawley rat (SD rat) was adopted and anaesthetized with 2% isoflurane, and then the right common carotid artery, external carotid artery and internal carotid artery were distinguished among them from the neck.

Next, a nylon monofilament with length of 22 millimeters (mm), size number of 4/0 and capped with polysiloxane was inserted into the external carotid artery and along with the external carotid artery to the circle of Willis to induce obstruction and ischemia in the middle cerebral artery. After causing obstruction and ischemia for 1 hour, the nylon monofilament was removed to allow the blood recirculated to the brain, in other words, to undergo blood reperfusion.

After blood reperfusion for 24 hours, the rat was sacrificed and the brain thereof was placed into a cooled 0.95% saline. Then, 1 mm part of the brain tip was excised, and the rest of the brain was cut in coronal section to obtain seven slices of brain tissue with each thickness of 2 mm. Next, those sliced brain tissues were infiltrated with 1% 2,3,5-triphenyltetrazolium chloride (TTC) for 30-minute at room temperature (about 25° C. to 27° C.). Afterward, the sliced brain tissues were stained with a 4% formalin solution, and then MacroPATH Digital Imaging System was used to record the images and the obtained images were analyzed by ImageJ 1.52a to count the infarct volume percent, which could represent the degree of nerve damage. The foresaid infarct volume percent was obtained by adding the values acquired by multiplying the proportion of infarct area of each sliced brain tissue with their thickness, and the proportion of infarct area was calculated by the equation: $(B-A)/B \times 100\%$; wherein, "A" represented the undamaged area in the damaged cerebral hemisphere on the right side, and "B" represented the total area of the undamaged cerebral hemisphere on the left side.

Here, 10 minutes before processing the foresaid MCAO/R model, the rats were administrated with the test samples of Examples 1 to 15 by intraperitoneal injection for one time. The administration amount was 50 milligrams per kilogram (mg/kg) or 5 ml/kg. The actual applied amount was depended on the weight of the rates. The treatment for the vehicle group was the same as that of the experimental group except only solvent was used.

The total infarct volume percent (sum of the infarct volume percent of the seven sliced brain tissues) of the groups of Examples 1 to 15, the vehicle group and the sham group were listed in the following Table 1 and FIG. 1. The results of TTC staining of the seven sliced brain tissues of the groups of Examples 1 to 15, the vehicle group and the sham group were shown in FIG. 2. 5 SD rats were used for each experimental groups of Examples 1 to 15 and the vehicle group, while only 3 SD rats were used for the sham group.

TABLE 2

The total infarct volume percent of Examples 1 to 15, the vehicle group, and the sham group.

| Groups | Total infarct volume percent (%) | Standard deviation |
| --- | --- | --- |
| Example 1 | 28.82 | 3.27 |
| Example 2 | 30.75 | 2.63 |
| Example 3 | 17.13 | 4.67* |
| Example 4 | 16.4 | 4.33* |
| Example 5 | 20.2 | 5.93 |
| Example 6 | 19.67 | 5.07* |
| Example 7 | 15.17 | 3.83** |
| Example 8 | 22.39 | 5.44 |
| Example 9 | 14.52 | 2.69*** |
| Example 10 | 21.76 | 2.40** |
| Example 11 | 15.93 | 5.71** |
| Example 12 | 35.67 | 4.82 |
| Example 13 | 32.53 | 2.11 |
| Example 14 | 34.77 | 7.00 |
| Example 15 | 17.76 | 4.06** |
| Vehicle group | 40.48 | 3.18 |
| Sham group | 1.79 | 0.15*** |

*p value less than 0.05,
**p value less than 0.01,
***p value less than 0.001

According to the results of Table 2, after the simulation of ischemic stroke and blood reperfusion for 24 hours, the total infarct volume percent was 40.48% for the vehicle group, which indicated that the foresaid simulation of ischemic stroke caused by the MCAO/R model actually led to extensive nerve damage. For the sham group, the total infarct volume percent was only 1.79%, which indicated that the nerve was not damaged, and the surgical operation during the experiment did not affect the result of the total infarct volume, and was statistically significant (p value less than 0.001) compared to the vehicle group.

From the data shown in Table 2, it indicated that all the Examples (1-15) had lower total infarct volume percent (about 14.52% to 35.76%) compared to that of the vehicle group. Furthermore, after analyzing those data by Student's T-test, it showed that the p values of Examples 3, 4 and 6 were less than 0.05; the p values of Examples 7, 10, 11 and 15 were less than 0.01; and the p value of Example 9 was less than 0.001; and that were statistically significant compared to that of the vehicle group. In addition, in FIG. 1, it could also be obviously observed that all the total infarct volume percent of Examples 1 to 15 were less than that of the vehicle group. Accordingly, administrating the novel compounds of the present invention in advance could actually reduce the total infarct volume percent, which indicated reducing the degree of nerve damage and thus having the effect of preventing nerve damage.

Figure 2:
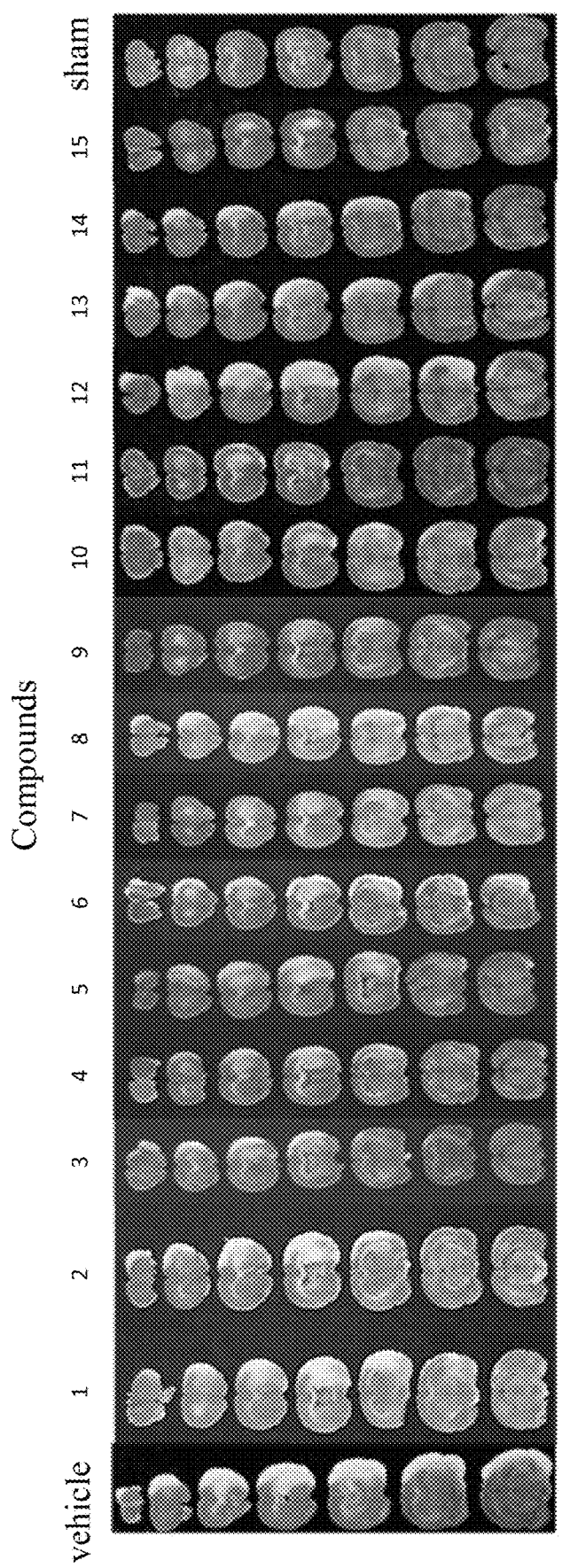
FIG. 2 is the results of staining different brain areas after the rats were administrated with the compounds of Examples 1 to 15.

According to FIG. 2, seven columns from top to bottom were respectively the staining results of the brain tissue slices which were 3 mm, 5 mm, 7 mm, 9 mm, 11 mm, 13 mm and 15 mm from the border of the brain of which, that 1 mm part of the brain tip was already excised. According to the principle of TTC staining, if any area of the brain tissue turned white, it meant that the nerve in that area was damaged. Referring to the staining result of the vehicle group, seven columns of the brain tissue slices showed apparent whiteness on the right side, which indicated that the nerves of different spots were actually damaged. However referring to the staining results of Examples 1 to 15, the whiteness on the right side of different spots of the brain tissue slices were not as obvious as that of the vehicle group, which could also verify that the novel compounds of the present invention actually had effect of preventing nerve damage.

Test Example 2: Neurobehavioral Evaluation

Figure 3:
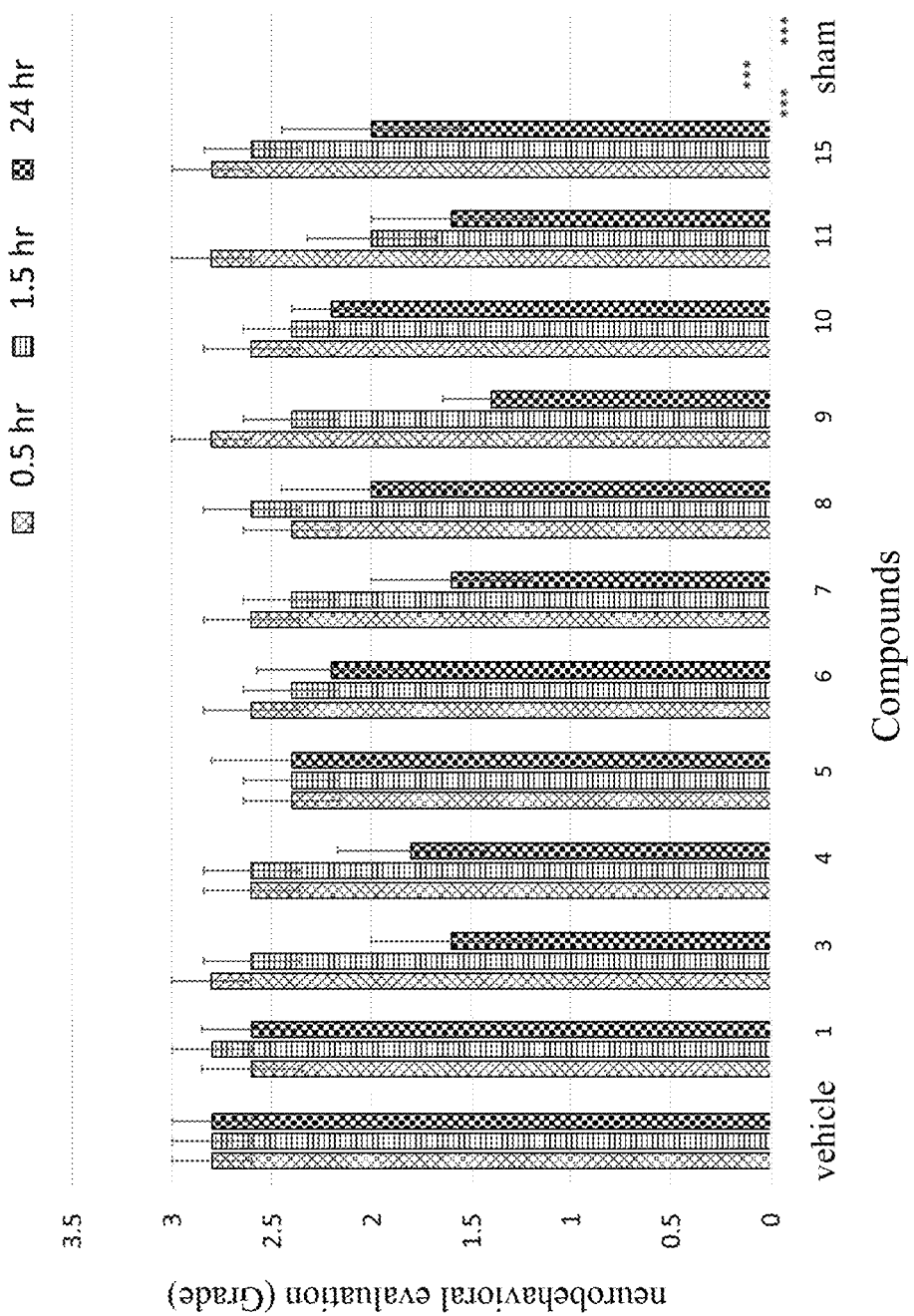
FIG. 3 is the results of neurobehavioral evaluation after the rats were administrated with the compounds of Examples 1, 3 to 11 and 15.

This test example and the foresaid Test example 1 were conducted simultaneously, and thus the preparation of the test samples, the vehicle group and the sham group were the same as those of Test example 1. Specifically, this test example adopted the compounds of Examples 1, 3 to 11 and 15, and the severity of nerve damage of the rat was evaluated according to the classification standards regulated by Bederson, so as to evaluate neurobehavior of the rat at the time interval of 0.5 hour, 1.5 hour and 24 hour after blood reperfusion of the MCAO/R model. The behavior evaluation and the corresponding classification of nerve damage was as the following: Grand 0, indicated the absence of nerve damage; Grade 1, indicated that the front limbs of the rat contracted to the contralateral side of the damaged brain area; Grade 2, indicated that the ability of resistance of the rat to the thrust was decreased at the ipsilateral side of the damaged brain area; Grade 3, indicated that the rat spontaneously circled toward the opposite side of the damaged brain area and could not go straight; and Grade 4, indicated severe nerve damage, that the limbs of the rat were weak and paralyzed or epilepsy occurred. The test results of compounds of Examples 1, 3 to 11 and 15, the vehicle group, and the sham group were listed in the following Table 3 and FIG. 3.

TABLE 3

The results of neurobehavioral evaluation of Examples 1, 3 to 11 and 15, the vehicle group, and the sham group.

| Groups | Time point of 0.5-hour after blood reperfusion | | Time point of 1.5-hour after blood reperfusion | | Time point of 24-hour after blood reperfusion | |
|---|---|---|---|---|---|---|
| | Grade | Standard deviation | Grade | Standard deviation | Grade | Standard deviation |
| Example 1 | 2.60 | 0.25 | 2.80 | 0.20 | 2.60 | 0.25 |
| Example 3 | 2.80 | 0.20 | 2.60 | 0.24 | 1.60 | 0.40 |
| Example 4 | 2.60 | 0.24 | 2.60 | 0.24 | 1.80 | 0.37 |
| Example 5 | 2.40 | 0.24 | 2.40 | 0.24 | 2.40 | 0.40 |
| Example 6 | 2.60 | 0.24 | 2.40 | 0.24 | 2.20 | 0.37 |
| Example 7 | 2.60 | 0.24 | 2.40 | 0.24 | 1.60 | 0.40 |
| Example 8 | 2.40 | 0.24 | 2.60 | 0.24 | 2.00 | 0.45 |
| Example 9 | 2.80 | 0.20 | 2.40 | 0.24 | 1.40 | 0.24 |
| Example 10 | 2.60 | 0.24 | 2.40 | 0.24 | 2.20 | 0.20 |
| Example 11 | 2.80 | 0.20 | 2.00 | 0.32 | 1.60 | 0.40 |
| Example 15 | 2.80 | 0.20 | 2.60 | 0.24 | 2.00 | 0.45 |
| Vehicle group | 2.80 | 0.20 | 2.80 | 0.20 | 2.80 | 0.20 |
| Sham group | 0.00 | 0.00 | 0.00 | 0.00 | 0.00 | 0.00 |

According to the results of Table 3, at the time interval of 0.5 hour, 1.5 hour and 24 hour after blood reperfusion, the Grades of neurobehavioral evaluation of the vehicle group were all 2.8 and close to the foresaid classification of Grade 3, which indicated that the neurobehavior was affected. However, according to the results of compounds of Examples 1, 3 to 11 and 15, all showed better results of neurobehavioral evaluation (all Grades less than 2.8). Moreover, at the time interval of 24 hour after blood reperfusion, the compounds of Examples 1, 3 to 11 and 15 showed even better results of neurobehavioral evaluation, and especially the results of neurobehavioral evaluation of the compounds of Examples 3, 4, 7, 9 and 11 were better than the foresaid classification of Grade 2. Besides, the results of FIG. 3 also showed that at the time interval of 24 hour after blood reperfusion, the neurobehavioral evaluation of Examples 1, 3 to 11 and 15 were actually better than those of the vehicle group. Accordingly, after administrating the novel compounds of the present invention, the condition of nerve damage could indeed be improved after a period of time.

Test Example 3: Evaluation of the Effect of Protecting Nerves

In this test, the compounds of Examples 1 to 15 were dissolved in DMSO to obtain the test solutions, and okadaic acid was used as never damage inducing agent for simulating the condition of neuron damage. Afterward, a cell counting kit, CCK-8 (purchased from Japanese Dojindo company) was used to evaluate the effect of the test sample for protecting nerves.

Specifically, mouse neuroblastoma cell line: Neuto-2a cell (ATCC®CCL-131') was adopted and cultured with MEM media containing 10 volume percent of fetal bovine serum (FBS) at 37° C. in an incubator filled with 5% corban dioxide. Then, the Neuro-2a cells were seeded in a 96-well plate with the cell density of 5*10³ cells/well. The volume of culture media was 100 microliters (μl) and the culture media contained 120 nM of okadaic acid. Then, the test solutions of Examples 1 to 15 were added one by one into the culture media, and the concentrations of the test solutions in the culture media were listed in the following Table 4. After co-treatment for 24 hours, the cell viability of each group was analyzed by CCK-8, and the group whose culture media contained only okadaic acid was set as the control group. The results of cell viability of each group were listed in the following Table 4. The experiment of each group was repeated 3 to 4 times.

TABLE 4

The results of cell viability of Examples 1 to 15 and the control group.

| Groups | Cell viability (%) | Standard deviation | Concentration |
|---|---|---|---|
| Example 1 | 45.50 | 2.94** | 0.01 μg/ml |
| Example 2 | 60.17 | 4.64** | 10 μg/ml |
| Example 3 | 54.07 | 1.46** | 0.01 μg/ml |
| Example 4 | 37.43 | 3.53 | 0.01 μg/ml |
| Example 5 | 67.27 | 6.12** | 0.1 μg/ml |
| Example 6 | 53.13 | 2.88** | 0.1 μg/ml |
| Example 7 | 61.03 | 5.68** | 0.1 μg/ml |
| Example 8 | 38.20 | 4.74 | 0.1 μg/ml |
| Example 9 | 44.84 | 3.78** | 0.1 μg/ml |
| Example 10 | 34.18 | 2.52 | 0.01 μg/ml |
| Example 11 | 39.11 | 4.86 | 0.01 μg/ml |
| Example 12 | 38.27 | 2.18* | 0.01 μg/ml |
| Example 13 | 39.90 | 1.74* | 0.1 μg/ml |
| Example 14 | 40.31 | 1.77* | 0.001 μg/ml |
| Example 15 | 36.75 | 4.41 | 0.1 μg/ml |
| Control group | 28.88 | 4.32 | 120 nM |

*p value less than 0.05,
**p value less than 0.01,
***p value less than 0.001

Figure 4:
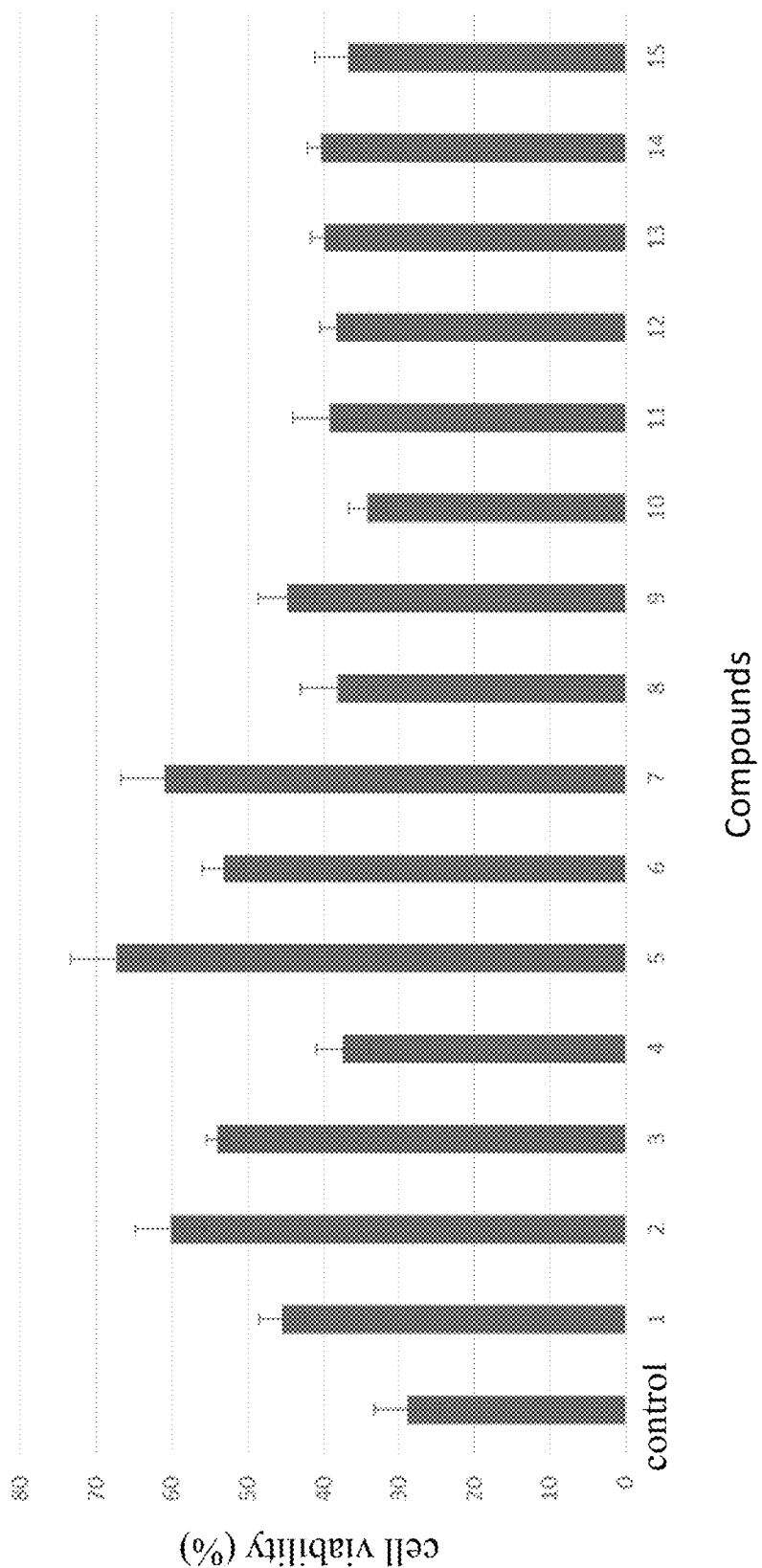
FIG. 4 is the experimental results of evaluating the effect of protecting nerves of the compounds of Examples 1 to 15.

According to the results of Table 4, the control group, which was only treated with okadaic acid, had cell viability of only 28.88%. However, in all the groups that were treated with the compounds of Examples 1 to 15, the cell viability (34.18% to 67.27%) was obviously higher than that of the control group, especially, for the compound of Example 5. Furthermore, after analyzing those results by Student's T-test, the results showed that Examples 1 to 3, 5 to 7, 9 to 12 and 14 were statistically significant compared to the control group, the p values of Examples 12 to 14 were less than 0.05; and the p values of Examples 1 to 3, 5 to 7 and 9 were less than 0.01. In addition, the results of cell viability of each group shown as diagram were listed in FIG. 4, and the results of the cell viability of Examples 1 to 15 were all higher than that of the control group could also be obviously observed. Accordingly, treatment of the novel compounds of the present invention at the time nerve damage occurred could actually raise the cell viability, which indicated that the compounds of the present invention could effectively reduce the degree of nerve damage and death, thereby having the effect of protecting nerves.

In conclusion, the present invention provides a novel compound and a preparation method thereof. The novel compound has effects of preventing nerve damage and protecting nerves, and thus can be used for preventing or improving the diseases caused by nerve damage, thereby providing patients with another highly potential and effective treatment method.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by the following Formula (I):

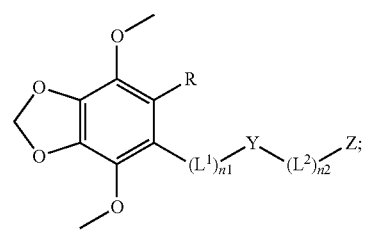

wherein, R is a hydrogen atom or an unsubstituted alkyl group having 1 to 6 carbon atoms;

L¹ is an unsubstituted alkylene group having 1 to 6 carbon atoms, and L² is an unsubstituted alkylene group having 1 to 6 carbon atoms or an unsubstituted arylene group having 6 to 18 carbon atoms;

Y is an acyloxy group or an amide group;

Z is a carboxyl group, pyrocatechin, an unsubstituted ester group having 1 to 6 carbon atoms, 2-methoxybenzenesulfonamide, 2,3-dimethyl-1-phenyl-5-pyrazolone, or 2-methyl-4-cyanothiophene; and n1 and n2 are each independently 0 or 1.

2. The compound as claimed in claim 1, wherein Z is a carboxyl group, pyrocatechin, —COOCH₂CH₃, 2-methoxybenzenesulfonamide, 2,3-dimethyl-1-phenyl-5-pyrazolone, or 2-methyl-4-cyanothiophene.

3. The compound as claimed in claim 1, wherein L² is an unsubstituted methylene group, an unsubstituted ethylene group, an unsubstituted propylene group, or an unsubstituted phenylene group.

4. A compound selected from the group consisting of:

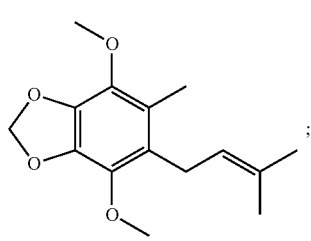

Compound 1

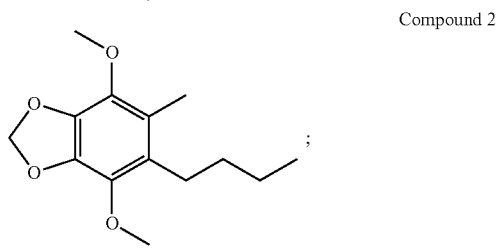

Compound 2

Compound 3
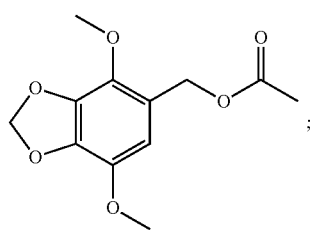
Compound 4
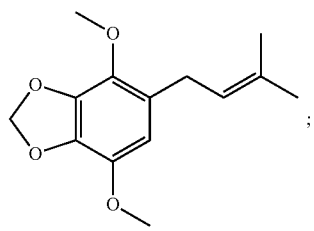
Compound 5
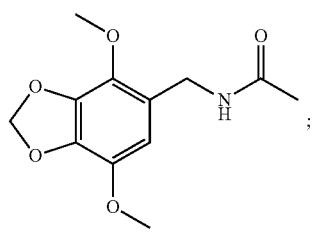
Compound 6
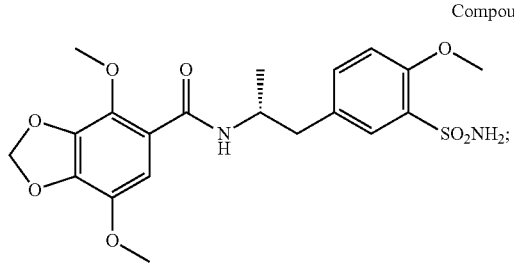
Compound 7
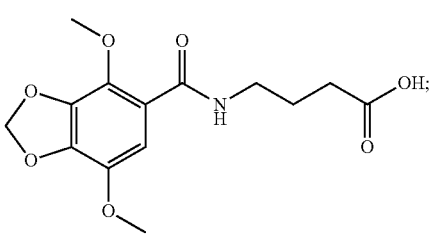
Compound 8
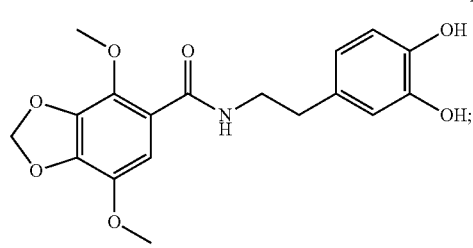
Compound 9
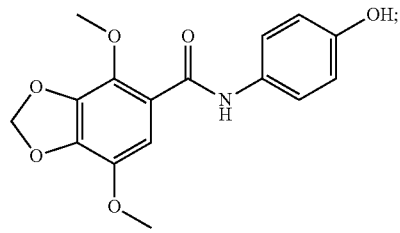
Compound 10
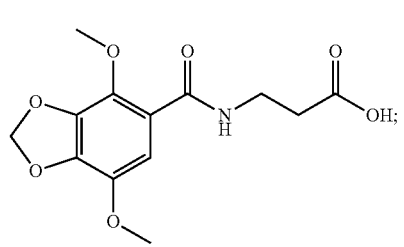
Compound 11
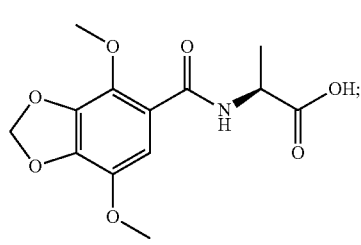 [SMILES: COc1cc(C(=O)N[C@@H](C)C(=O)O)c(OC)c2c1OCO2]
Compound 12
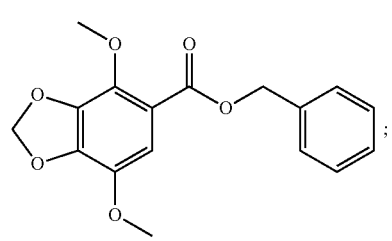
Compound 13
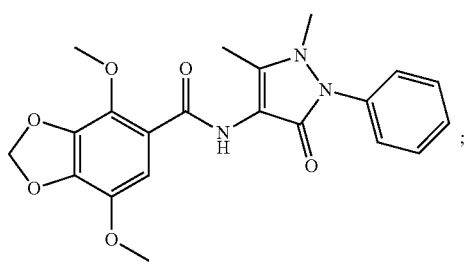
Compound 14
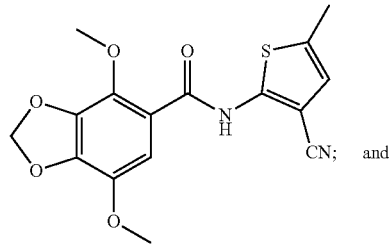
and -continued Compound 15

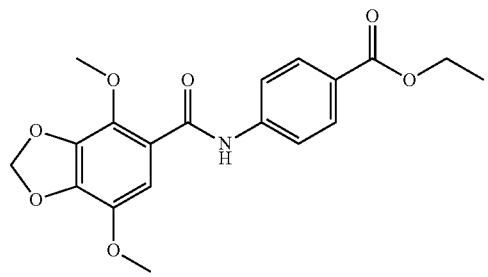 [SMILES: CCOC(=O)c1ccc(NC(=O)c2cc(OC)c3c(c2OC)OCO3)cc1]

5. A preparation method of the compound as claimed in claim 4, comprising the following steps:

step (a): providing a first reactant, wherein the first reactant step (b): providing a second reactant, wherein the second reactant comprises 4,7-dimethoxy-5-methyl-6-iodo-1,3-benzodioxole, 4,7-dimethoxy-5-iodo-1,3-benzodioxole, 4,7-dimethoxy-5-hydroxymethyl-1,3-benzodioxole, 4,7-dimethoxy-5-aminomethyl-1,3-benzodioxole, 4,7-dimethoxy-1,3-benzodioxole-5-carboxylic acid, or 4,7-dimethoxy-5-acylchloride-1,3-benzodioxole;

step (b): providing a second reactant, wherein the second reactant comprises 3,3-dimethylallyl bromide, 1-bromobutane, acetic anhydride, and 4-aminophenol phenylmethanol, ethyl p-aminobenzoate, 5-[(R)-(2-aminopropyl)]-2-methoxy-benzenesulfonamide, 4-aminobutyric acid methyl ester hydrochloride, β-alanine methyl ester hydrochloride, alanine methyl ester hydrochloride, 4-(2-aminoethyl)-1,2-benzenediol hydrochloride, 4-aminoantipyrine, or 2-amino-3-cyano-5-methylthiophene; and step (c): reacting the first reactant with the second reactant to obtain the compound.

6. The preparation method as claimed in claim 5, wherein the first reactant is 4,7-dimethoxy-5-acylchloride-1,3-benzodioxole, and the step (a) further comprises a step of subjecting 4,7-dimethoxy-1,3-benzodioxole-5-carboxylic acid by chlorination to form 4,7-dimethoxy-5-acylchloride-1,3-benzodioxole in advance, thereby obtaining the first reactant.

7. The preparation method as claimed in claim 5, wherein the first reactant is 4,7-dimethoxy-5-acylchloride-1,3-benzodioxole and the second reactant is ester hydrochloride derivative, and the step (c) further comprises steps of reacting the first reactant with the second reactant to obtain a methyl ester intermediate, and then subjecting the methyl ester intermediate to hydrolysis to obtain the compound.

8. A pharmaceutical composition for preventing nerve damage and protecting nerves, comprising the compound as claimed in claim 1 and a pharmaceutically acceptable carrier.

9. A method for preventing nerve damage and protecting nerves, comprising administration of a therapeutically effective amount of the compound as claimed in claim 5.

10. The method as claimed in claim 9, wherein preventing nerve damage and protecting nerves comprises preventing and/or treating stroke and Alzheimer's disease.

11. A pharmaceutical composition for preventing nerve damage and protecting nerves, comprising the compound as claimed in claim 4 and a pharmaceutically acceptable carrier.

* * * * *